(12) United States Patent
Ben-Shahar

(10) Patent No.: US 9,429,773 B2
(45) Date of Patent: Aug. 30, 2016

(54) METHOD AND APPARATUS FOR DESIGN AND FABRICATION OF CUSTOMIZED EYEWEAR

(71) Applicant: Adi Ben-Shahar, Santa Monica, CA (US)

(72) Inventor: Adi Ben-Shahar, Santa Monica, CA (US)

( * ) Notice: Subject to any disclaimer, the term of this patent is extended or adjusted under 35 U.S.C. 154(b) by 44 days.

(21) Appl. No.: 13/797,182

(22) Filed: Mar. 12, 2013

(65) Prior Publication Data

US 2014/0268007 A1    Sep. 18, 2014

(51) Int. Cl.
*G02C 7/02* (2006.01)
*G02C 13/00* (2006.01)
*G02C 5/00* (2006.01)

(52) U.S. Cl.
CPC ............ *G02C 13/003* (2013.01); *G02C 5/001* (2013.01); *G02C 7/027* (2013.01)

(58) Field of Classification Search
CPC .......... G02C 7/00; G02C 7/02; G02C 7/024; G02C 7/027; G02C 2202/06; G02C 5/00; G02C 5/001; G02C 5/008
USPC ............ 351/159.01, 159.74–159.77, 159.81, 351/83, 178
See application file for complete search history.

(56) References Cited

U.S. PATENT DOCUMENTS

| | | | |
|---|---|---|---|
| 1,003,889 A | 9/1911 | Edmonds | |
| 1,891,036 A * | 12/1932 | Albitz | 351/159.75 |
| 2,537,047 A * | 1/1951 | Gatten | 351/159.02 |
| 4,761,196 A | 8/1988 | Brown et al. | |
| 5,247,706 A | 9/1993 | Mark | |
| 5,576,778 A | 11/1996 | Fujie et al. | |
| 5,592,248 A * | 1/1997 | Norton et al. | 351/246 |
| 5,657,106 A | 8/1997 | Herald, Jr. et al. | |
| 6,142,628 A | 11/2000 | Saigo | |
| 6,682,195 B2 | 1/2004 | Dreher | |

(Continued)

FOREIGN PATENT DOCUMENTS

WO   WO 0023021    4/2000
WO   WO 03079097   9/2003

(Continued)

OTHER PUBLICATIONS

Adam, Brian, Measuring Yourself for Eyeglasses, http://www.adam.co.nz/eyewear/custom_eyeglasses/measuring.htm, printed on Mar. 13, 2014 (5 pages).

(Continued)

*Primary Examiner* — Huy K Mai
(74) *Attorney, Agent, or Firm* — Knobbe, Martens, Olson & Bear, LLP

(57) ABSTRACT

Eyewear can include lenses having perimeters that are customized for an intended wearer. The perimeter of the lenses can be determined based on anatomical features of the wearer's face, the wearer's field of vision, or other parameters specific to that individual. Determination of the lens perimeters can involve developing a three-dimensional model of a wearer's face and/or head, demarcating a lens perimeter over an obtained image of a user's face, or delineating the boundary of a wearer's peripheral vision. A provisional lens perimeter obtained by any of these methods may be modified in curvature and/or size to arrive at a desired final lens perimeter. Customized lenses can be fabricated based on the determined lens perimeters. The customized lenses can be assembled into completed eyewear that is customized for a wearer, for example having shapes, sizes, and designs not otherwise possible.

79 Claims, 15 Drawing Sheets

(56) References Cited

U.S. PATENT DOCUMENTS

| | | |
|---|---|---|
| 7,434,931 B2 | 10/2008 | Warden |
| 7,651,217 B2 | 1/2010 | Welchel et al. |
| 7,677,724 B1 | 3/2010 | Erickson et al. |
| 7,845,797 B2 | 12/2010 | Warden |
| 8,220,923 B2 | 7/2012 | Saffra |
| 2002/0159024 A1 | 10/2002 | Chang |
| 2003/0081173 A1 | 5/2003 | Dreher |
| 2003/0090625 A1 | 5/2003 | Izumitani et al. |
| 2003/0169494 A1 | 9/2003 | Porter et al. |
| 2005/0162419 A1 | 7/2005 | Kim et al. |
| 2008/0129952 A1 | 6/2008 | Jannard et al. |
| 2008/0316605 A1 | 12/2008 | Hazell et al. |
| 2009/0066914 A1 | 3/2009 | Moinard |
| 2010/0026955 A1 | 2/2010 | Fisher et al. |
| 2016/0103335 A1 | 4/2016 | Ben-Shahar |

FOREIGN PATENT DOCUMENTS

| | | |
|---|---|---|
| WO | WO 03081536 | 10/2003 |
| WO | WO 2005/071468 A1 | 8/2005 |
| WO | WO 2005071468 | 8/2005 |
| WO | WO 2014164347 | 10/2014 |

OTHER PUBLICATIONS

Correct Measurements for Your Eye Glasses, http://optometrist.com.au/correct-measurements-eye-glasses/, Jun. 28, 2012 (4 pages).

Custom-made Glasses, http://www.maisonbonnet.com/en/custom-made-glasses, web page as of Jan. 1, 2012, retrieved from the wayback machine (web.archive.org) on Mar. 13, 2014 (2 pages).

Mochimaru and Kauchi, Technologies for the Design and Retail Service of Well-fitting Eyeglass Frames, *Synthesiology*—english edition vol. 1, No. 1, p. 38-46 (2008) (9 pages).

Thomas, Liana, How to Determine the Size of Glass Frames, http://www.ehow.com/how_8337112_determine-size-glass-frames.html, printed on Mar. 13, 2014.

International Search Report and Written Opinion in International App. No. PCT/Us2014/022001, dated Jul. 4, 2014.

Non-final Office Action dated Apr. 7, 2016 for U.S. Appl. No. 14/852,427.

Meister, et al., "Introduction to Ophthalmic Optics", Carl Zeiss Vision, 1999.

OptiCampus.com; Online Optical Continuing Education; OptiCampus Optical Calculators; Lens Thickness Calculation, http://www.opticampus.com/tools/thickness.php, web page as of Mar. 23, 2006, retrieved from the wayback machine (https://archive.org/web/) on Apr. 18, 2016.

\* cited by examiner

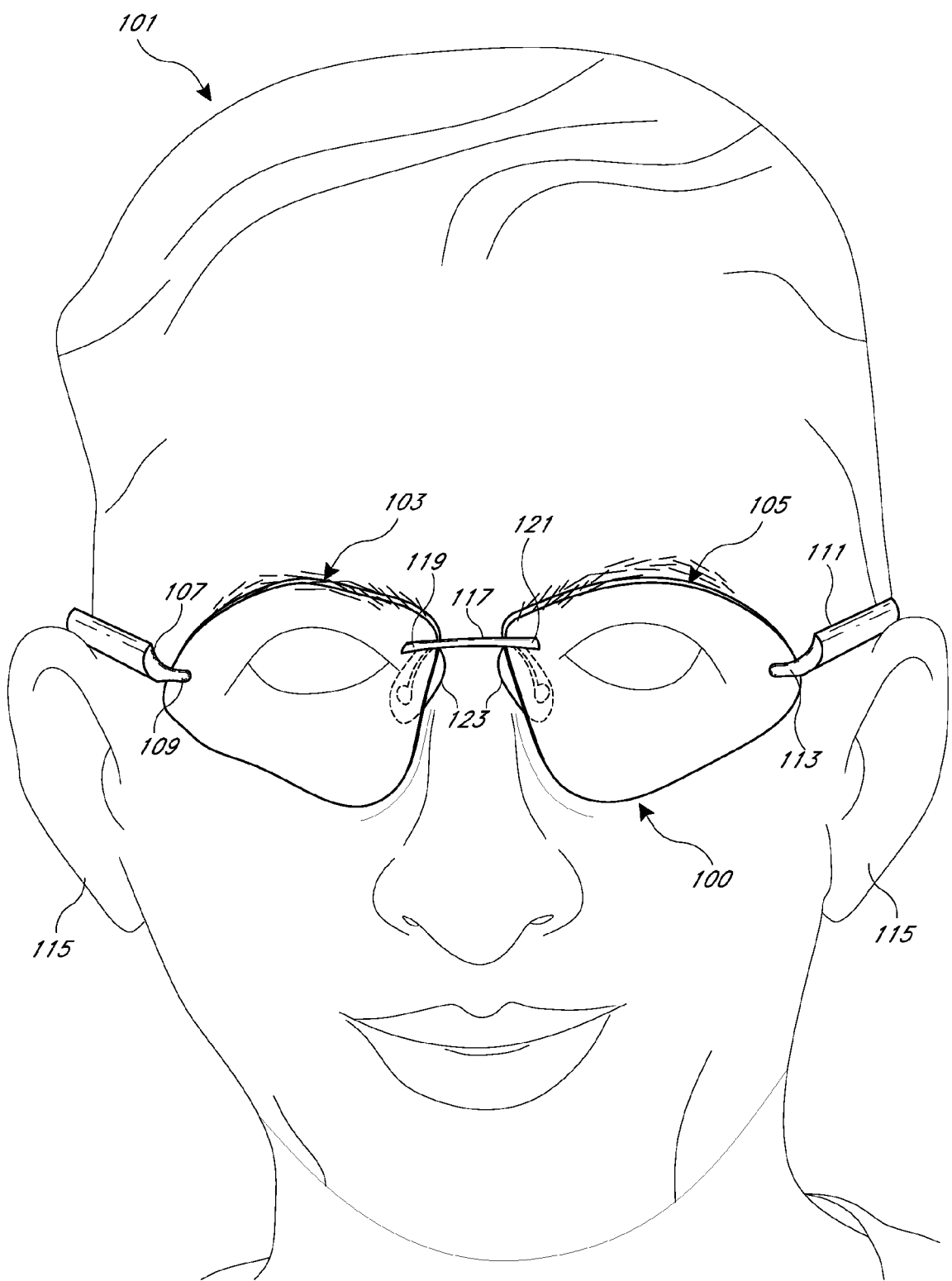
FIG. IA

505a

505b

505c

505d

505e

METHOD AND APPARATUS FOR DESIGN AND FABRICATION OF CUSTOMIZED EYEWEAR

BACKGROUND

1. Field of the Invention

Embodiments of the present disclosure relate to eyewear, and especially eyewear customized for a wearer.

2. Description of the Related Art

Eyewear has a wide variety of applications, including optical correction, safety (such as in construction or sports), aesthetics, shading the eyes from sunlight, and viewing three-dimensional images or video.

In each of these applications, eyewear is typically mass-produced with little or no customization. At most, a consumer may select from a variety of off-the-shelf eyewear designs and have lenses shaped for optical prescription. However, the shape and dimensions of the face, as well as the field of vision, vary widely from one individual to the next, and it may therefore be beneficial to provide eyewear that is customized to the wearer's face, field of vision, or other parameters specific to that individual.

SUMMARY OF THE INVENTION

The systems, methods and devices of the disclosure each have several innovative aspects, no single one of which is solely responsible for the desirable attributes disclosed herein.

In one aspect customized eyewear can comprise: a first lens having a front surface, a back surface, and a perimeter, wherein the perimeter is customized for a wearer; and a second lens having a front surface, a back surface, and a perimeter, wherein the perimeter is customized for the wearer.

In some embodiments, the perimeters of the first and second lenses can each be customized for the wearer on the basis of one or more of: peripheral vision of the wearer; shape of the wearer's nose; curvature of the wearer's face; and shape or location of the wearer's orbits. In some embodiments, the perimeters of the first and second lenses can each be further customized for the wearer on the basis of non-physical attributes of a wearer. In some embodiments, the eyewear can be rimless. In some embodiments, the eyewear can further comprise a frame that supports the first and second lenses, wherein the frame is configured to hold the first and second lenses against at least a portion of the wearer's face in a first position. In some embodiments, in the first position at least one of the first and second lenses is in contact with the wearer's face. In some embodiments, the first and second lenses are configured such that when the frame is in the first position against the wearer's face, the wearer cannot view the perimeter of the first lens or the perimeter of the second lens. In some embodiments, the first lens has optical power. In some embodiments, the perimeter of the first lens encloses a larger or smaller area than the perimeter of the second lens. In some embodiments, the first lens and the second lens are asymmetrical with respect to one another.

In accordance with another aspect, a method for producing customized eyewear comprises: obtaining one or more parameters of a wearer's face or field of vision; determining a perimeter of a first lens based on the one or more parameters; and determining a perimeter of a second lens based on the one or more parameters.

In some embodiments, the method can further comprise storing the determined perimeters of the first and second lenses. In some embodiments, the method can further comprise transmitting the stored perimeters to an optical laboratory (lab). In some embodiments, the method can further comprise fabricating the first and second lenses based on the determination of the perimeters. In some embodiments, the determining the perimeters of the first and second lenses can comprise: determining a provisional perimeter of the first lens; determining a provisional perimeter of the second lens; comparing the provisional perimeters of the first and second lenses; determining a final perimeter of a first lens based on the comparison; and determining a final perimeter of the second lens based on the comparison. In some embodiments, the provisional perimeters of the first and second lenses can be asymmetrical with respect to one another, and the final perimeters of the first and second lenses can be symmetrical with respect to one another. In some embodiments, determining the final perimeters of the first and second lenses can comprise obtaining an average the provisional perimeters of the first and second lenses. In some embodiments, determining the final perimeters of the first and second lenses can comprise adjusting the provisional perimeters based on non-physical attributes of the wearer. In some embodiments, obtaining one or more parameters comprises measuring dimensions of the wearer's face. In some embodiments, the dimensions can comprise one or more of: shape of the wearer's nose; curvature of the wearer's face; and shape or location of the wearer's orbits. In some embodiments, measuring dimensions of the wearer's face can comprise using images of the wearer's face to create a three-dimensional model of the wearer's face. In some embodiments, obtaining one or more parameters can comprise obtaining an image of the wearer's face, and determining the perimeters of the first and second lenses can comprise delineating the perimeters with respect to the obtained image. In some embodiments, delineating the perimeters can comprise drawing the perimeters over the obtained image. In some embodiments, obtaining one or more parameters can comprise measuring the peripheral vision of an eye of the wearer. In some embodiments, measuring the peripheral vision can comprise identifying a point at which the eye cannot view an object positioned about the periphery of the field of vision of the eye. In some embodiments, the point can be at a position nearest the eye's field of vision at which the eye cannot view the object. In some embodiments, measuring the peripheral vision can comprise identifying a plurality of such points, and extrapolating to develop a line circumscribing the eye, the line defining a boundary of the field of vision of the eye. In some embodiments, the perimeter of the first lens corresponds to the line.

In accordance with another aspect, a method for producing customized eyewear can comprise: receiving dimensions of a perimeter of a first lens, the perimeter being customized for a wearer; receiving dimensions of a perimeter of a second lens, the perimeter being customized for the wearer; and fabricating first and second lenses based on the received dimensions.

In some embodiments, the perimeters of the first and second lenses can be determined based on one or more parameters of a wearer's face or field of vision. In some embodiments, the method can further comprise assembling the first and second lenses in a frame. In some embodiments, the frame can be customized for the wearer. In some embodiments, the method can comprise fabricating only less than 10 lenses based on the received dimensions. In some embodiments, the method can comprise fabricating only less than 5 lenses based on the received dimensions.

BRIEF DESCRIPTION OF THE DRAWINGS

FIGS. 1A and 1B are front and side views of an example of customized eyewear on a wearer.

DETAILED DESCRIPTION OF THE PREFERRED EMBODIMENT

The following description is directed to certain embodiments for the purposes of describing the innovative aspects of this disclosure. However, a person having ordinary skill in the art will readily recognize that the teachings herein can be applied in a multitude of different ways. The described embodiments may be implemented in any device or system that can be configured to provide visualization of a surgical site. Thus, the teachings are not intended to be limited to the embodiments depicted solely in the figures and described herein, but instead have wide applicability as will be readily apparent to one having ordinary skill in the art.

Figure 1B:
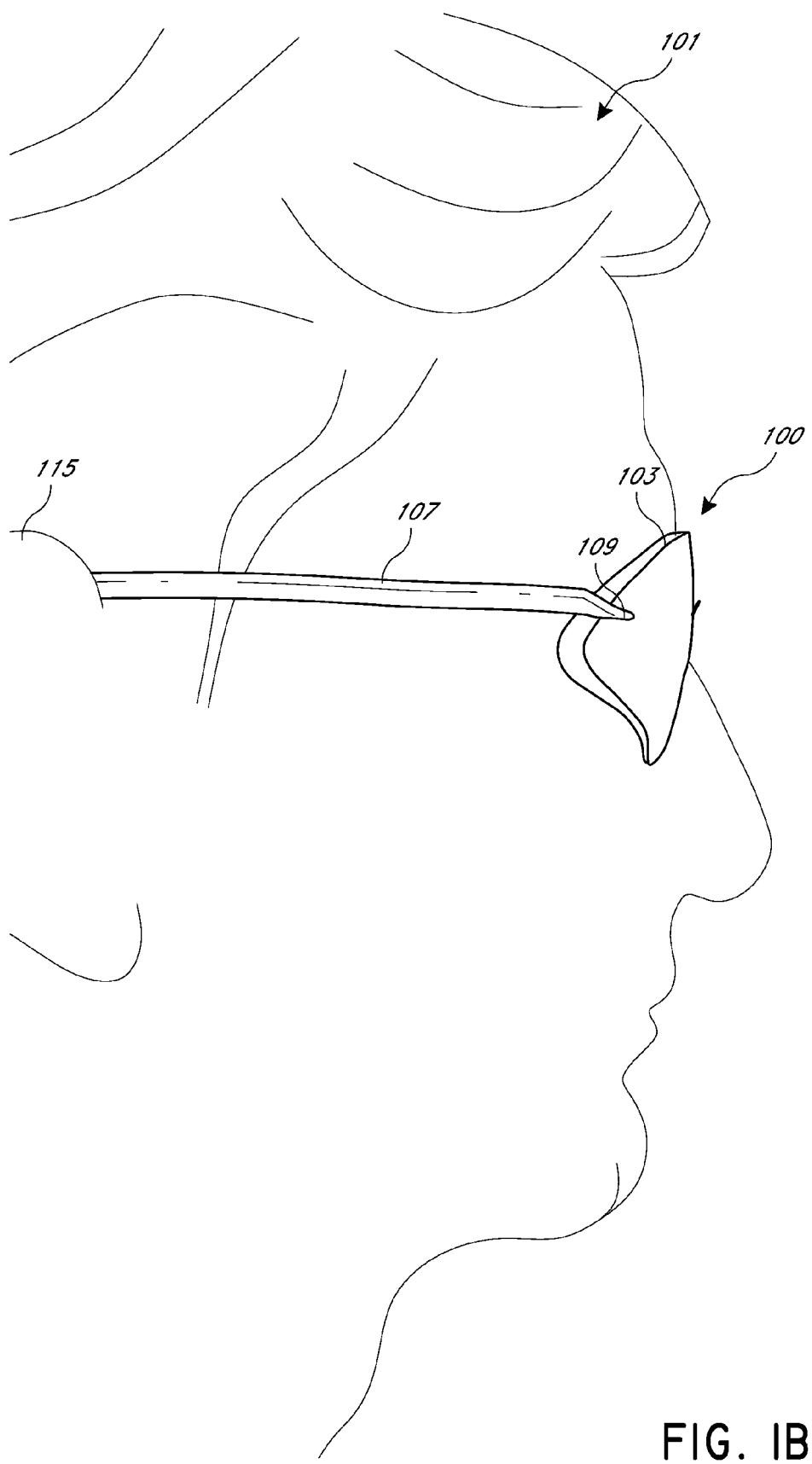

FIGS. 1A and 1B are front and side views of customized eyewear on a wearer. The eyewear 100 is illustrated here as worn by an individual 101. The eyewear 100 is a dual lens configuration including a right lens 103 and left lens 105 (with left and right here defined from the perspective of the wearer 101). Right temple 107 is coupled to the right lens 103 at connection point 109, while left temple 111 is coupled to the left lens 105 at connection point 113. Each of the temples 107 and 111 extend rearwardly from their respective connection points 109 and 113 on the lateral sides of the lenses to the wearer's ears 115. In some embodiments, a hinge can be positioned at each of connection points 109 and 113, which permits the temples 107 and 111 to be folded inward towards the lenses 103 and 105. A bridge 117 extends between a connection point 119 of the right lens 103 to a connection point 121 of left lens 105. Nose pads 123 are positioned near the medial portion of the lenses 103 and 105, and can be coupled to the bridge 111. In the illustrated embodiment, the eyewear 100 is rimless. However, as described in more detail below, in other embodiments the eyewear may have full or partial rims. In some embodiments, the dual lens configuration can be replaced with a unitary or shield-type lens, for example as often used in goggles.

Each of the lenses 103 and 105 include a front surface, a back surface, and an edge extending between the front and back surfaces. The contour of the edge defines the perimeter of each lens as a closed loop in two or three-dimensional space. As seen in FIG. 1B, the lateral portion of the right lens 103 in the illustrated embodiment extends rearward and tapers to partially "wrap around" the face of the wearer 101. In other embodiments, the lens may be substantially flat or assume other shapes.

One or both of the lenses may have optical power (e.g., corrective lenses, reading glasses), or conversely may be without optical power. In some embodiments, one or both of the lenses can be polarized, or tinted (for example colored or darkened) to protect the wearer's eyes from sunlight or other bright lights. In some embodiments, one or both of the lenses can be made of glass, plastic (such as CR-39), polycarbonate, Trivex®, or other transparent or partially transparent material. In some embodiments, one or both lenses may be treated with an optical coating, such as antireflective coating, high-reflective coating, and scratch-resistant coating. In some embodiments, one or both of the lenses may have an optical power consistent with a prescription from an optometrist or ophthalmologist. For example, the prescription may indicate the power to which each lens should be made in order to alleviate the effects of refractive errors, including myopia (nearsightedness), hypermetropia (farsightedness), astigmatism, and presybopia. In some embodiments, one or both lenses may be bifocals having two distinct optical powers in a single lens. In some embodiments, one or both lenses may be trifocals having three distinct optical powers in a single lens. In some embodiments, one or both lenses can be progressive, having a graduated optical power across the lens.

The perimeters of the lenses may assume a wide variety of shapes. In some embodiments, the perimeter of each lens is based on one or more parameters of an intended wearer (for example, an optometry patient). For example, in some embodiments, the perimeter of each lens may be shaped such that, when worn by the intended wearer, the perimeter substantially tracks the outer limits of the wearer's field-of-vision. In this configuration, the perimeters of the lenses may be such that, when worn by the intended wearer, the lenses cover the wearer's entire field-of-vision and the edges of the lenses are not visible to the wearer. In some embodiments, the perimeters may be shaped to correspond to only a portion of the limits of the wearer's field-of-vision. In some embodiments, the perimeters may not be shaped to correspond to any portion of the limits of the wearer's field-of-vision, but rather may be shaped based on other features of the intended wearer.

In some embodiments, the perimeter of each lens may be shaped to correspond to certain anatomical features of the intended wearer's face. For example, the medial edge of the lens may be shaped to follow the contours of the wearer's nose. In some embodiments, the superior edge of the lens may be shaped to follow the contours of the supraorbital arch (i.e., the eyebrow bone) of the intended wearer. In some embodiments, the inferior (lower) and lateral (side) edges of the lens may be shaped to follow the lateral and inferior contours of the orbit (including, for example, the frontal bone, zygomatic bone, and maxillary bone). Various other configurations are possible. For example, the perimeters may be shaped to correspond not to skeletal features, but to superficial anatomical features, such as the wearer's eyebrows, eyelashes, a scar, birth mark, or other feature of a wearer's face. Additionally, the shape of the perimeters may depend in part on the size and shape of the wearer's facial muscles (e.g., frontalis, procerus, orbicularis oculi, zygomaticus), the size and shape superficial fat compartments of the wearer's face (e.g., superior orbital, inferior orbital, lateral orbital, lateral temporal-cheek, central, nasolabial), or other anatomical features of the wearer's face or head. The perimeters may be customized for particular applications. For example, safety eyewear can have lenses customized to protect the wearer's eyes from incoming projectiles or radiation from any direction. Similarly, the lens perimeters may be customized to block wind from reaching a wearer's eyes. In some embodiments, the perimeter of the lens may be shaped at least in part based on aesthetic or stylistic considerations.

In addition to customization of the lens perimeters, the points of connection to the temples and bridge may additionally be customized for a wearer. For example, the dimensions of the nasal bridge may affect both the size of the bridge 111 and the location of connection points 119 and 121. Additionally, the location of connection points 109 and 113 between the temples and the lenses can be customized based on the location of the wearer's ears 115. In some embodiments, the right and left lenses may be asymmetrical, with respect to one or more of the perimeter, connection point to temples, and connection point to the bridge. In some embodiments, the perimeters of asymmetrical lenses may enclose areas of differing sizes. The human face is typically asymmetrical. Accordingly, depending on which features are used for the customization, the right and left lenses may be asymmetrical. Additionally, the height of the left and right ears may not be identical, and accordingly the position of the connection points 109 and 111 may be asymmetrical between the two lenses. In some embodiments, the lenses may be symmetrical with respect to one or more of the perimeter, connection point to temples, and connection point to the bridge. The use of customized lenses may allow for bridge and temples having designs and shapes that are otherwise not possible or practical when the shape of the lens is pre-existing.

The customization of lens perimeters, points of connection to temples and bridge, and frame represents a fundamentally different approach to the sale, design, and fabrication of eyeglasses as compared with current industry practice. In the conventional approach, the frames are typically mass produced and designed to retain lenses having a given perimeter. The lens blanks are also typically mass produced. To produce individual prescription eyewear, for example, lenses are obtained by selecting an appropriate blank and modifying as needed to produce the desired optical power. A lens having a perimeter that matches the frame or is otherwise standard for the selected eyewear model, is cut from the lens blank (edged) and mounted in the standard frame or otherwise integrated into the eyewear. As described in more detail below, the present disclosure describes an approach that is radically different. Rather than searching for pre-made glasses of a given shape that best fit the wearer's physical and/or aesthetic attributes and requirements, the glasses may be custom fabricated and shaped to fit the wearer's physical and aesthetic attributes and requirements. By starting with measurements of the wearer's face and/or field of vision, eyewear can be produced that is tailor made to the individual wearer, potentially providing superior fit and functionality.

Figure 2A:
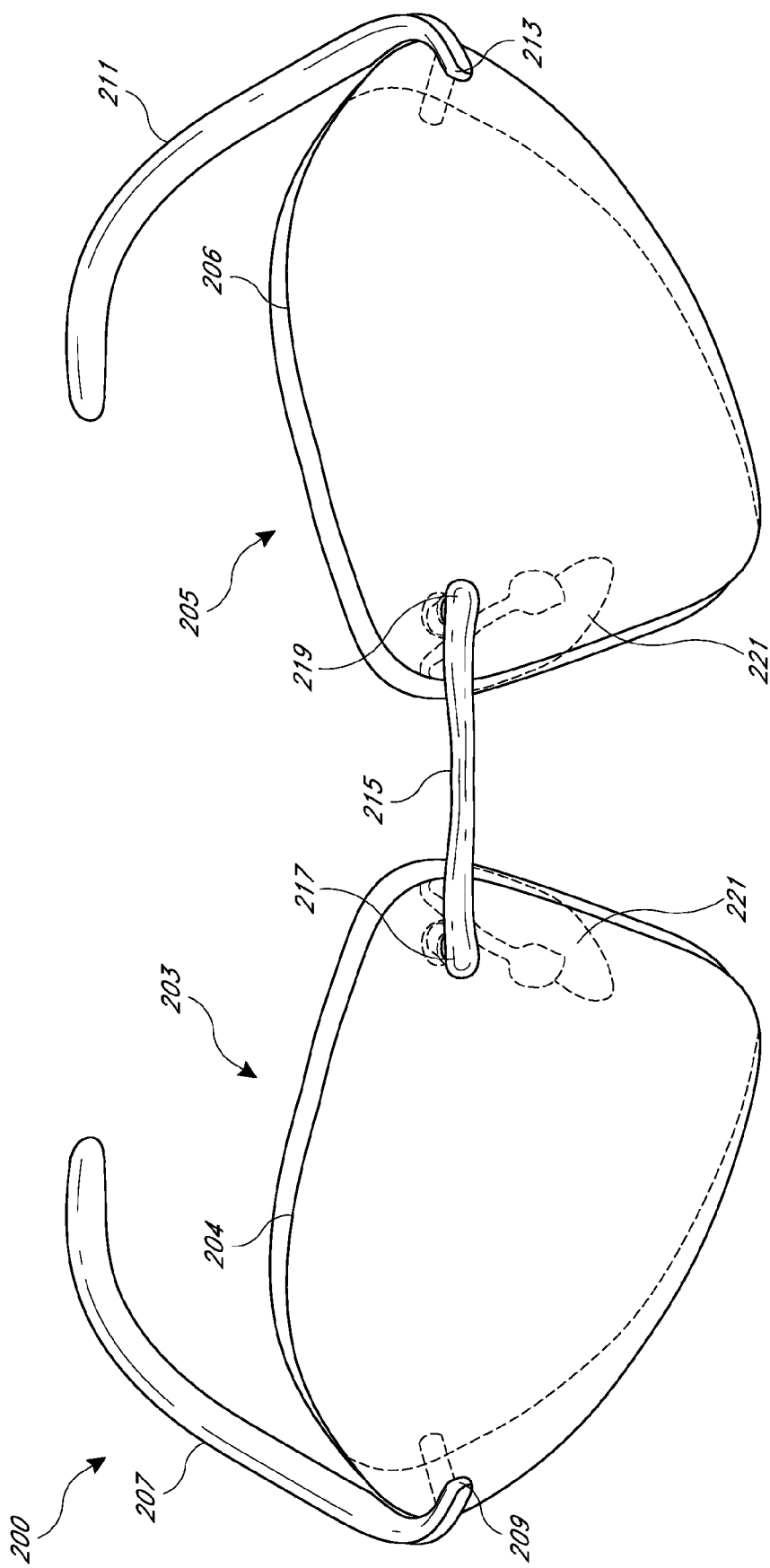
FIG. 2A is a front perspective view of rimless customized eyewear.
Figure 2B:
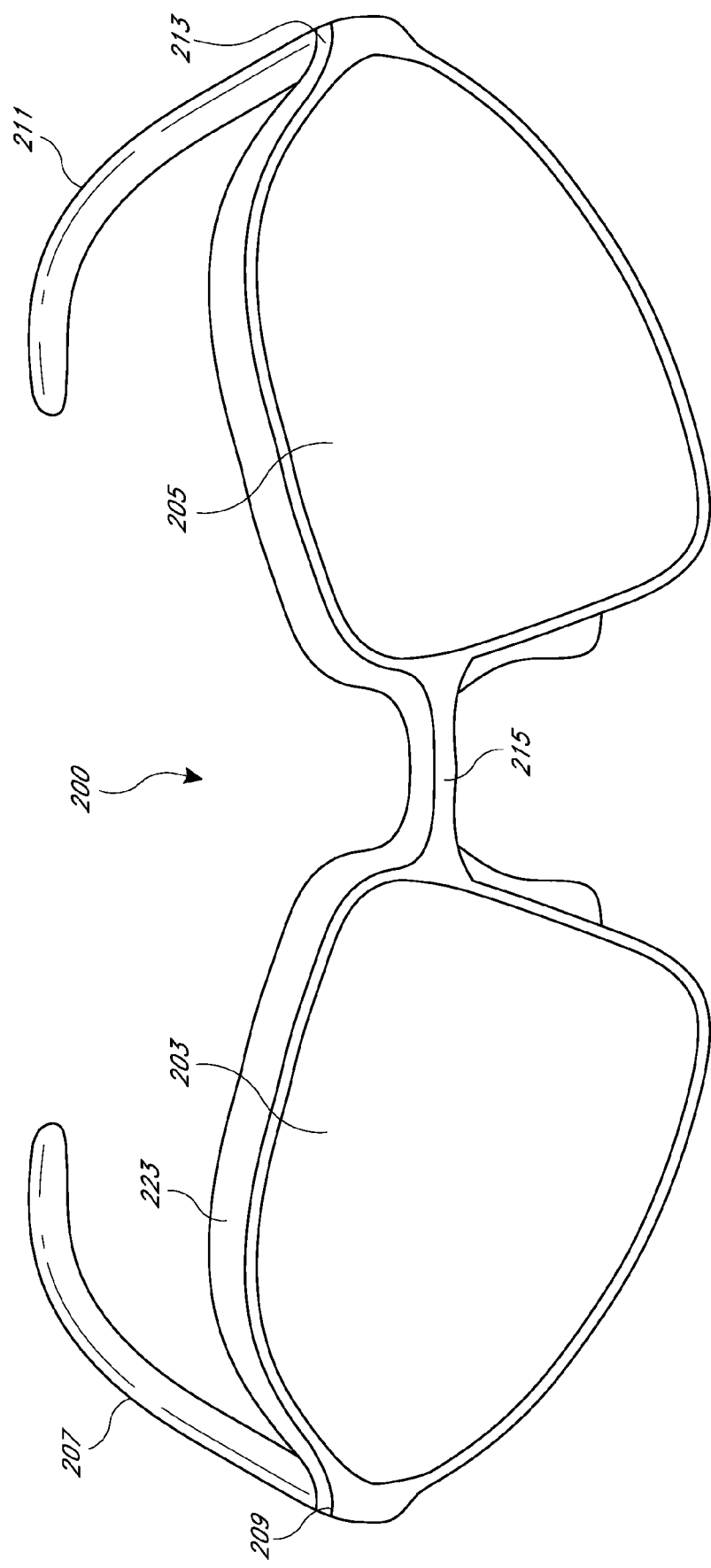
FIG. 2B is a front perspective view of full rim customized eyewear.
Figure 2C:
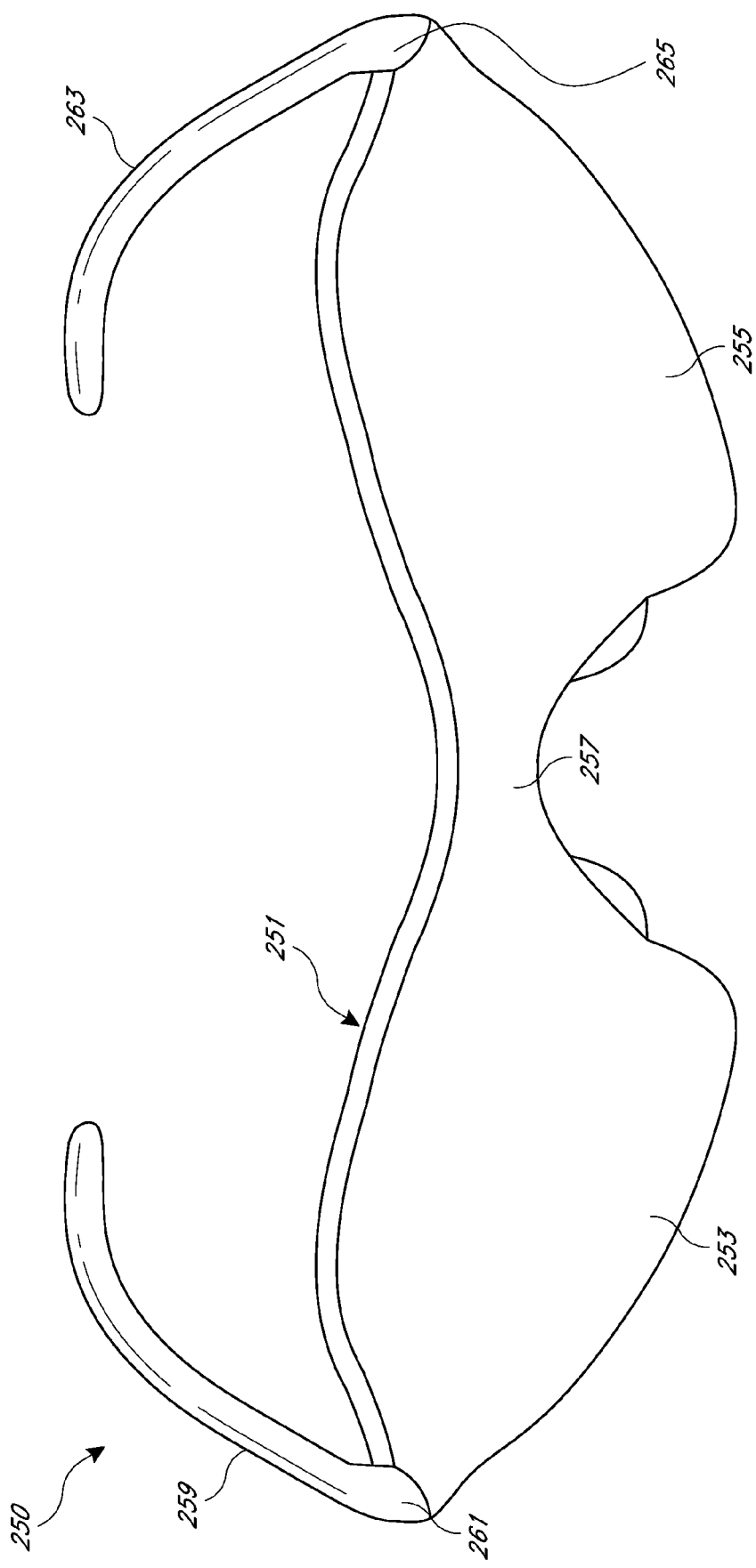
FIG. 2C is a front perspective view of customized eyewear having a unitary or shield-type lens.

FIGS. 2A-2C are front perspective views of different embodiments of customized eyewear. With respect to FIG. 2A, the eyewear 200 having a dual lens configuration includes a right lens 203 and a left lens 205. As described above with respect to FIGS. 1A and 1B, each of the lenses includes a front surface, a back surface, and an edge extending between the front and back surfaces. Edge 204 defines the perimeter of the right lens 203, while edge 206 defines the perimeter of left lens 205. The contours of these edges define the perimeter of each lens as a closed loop in three-dimensional space. Right temple 207 is coupled to the right lens 203 at connection point 209, while left temple 211 is coupled to the left lens 205 at connection point 213. A bridge 215 extends between a connection point 217 of the right lens 203 to a connection point 219 of left lens 205. Nose pads 221 are positioned near the medial portion of the lenses 203 and 205, and are be coupled to the bridge 211. In the illustrated embodiment, the eyewear 100 is rimless.

FIG. 2B illustrates eyewear 200 that is similar to that illustrated in FIG. 2A, except that the right and left lenses 203 and 205 are retained in a frame 223 having full rims. In this embodiment the frame 223 includes a bridge portion 215. Right temple 207 is coupled to the right lateral edge of the frame 223 at connection point 209, and left temple 211 is coupled to the left lateral edge of frame 223 at connection point 213. In some embodiments, a hinge can be positioned at each of connection points 209 and 213, which permits the temples 207 and 211 to be folded inward towards the lenses 103 and 105. The frame 223 may assume a variety of shapes and be made from a variety of materials. For example, in various embodiments the frame 223 can be made of plastic, metal, metal alloys, rubber, or other suitable material. The frame 223 can assume various thicknesses depending on the application in addition to aesthetic or stylistic considerations. Although the illustrated embodiment shows a frame 223 that fully circumscribes each lens 203 and 205, in other embodiments a frame may only partially surround each lens. For example, a frame may only follow the superior edge of the lenses, while the lateral, medial, and inferior edges may not be surrounded by the frame. In some embodiments, the frame may be flexible, and can be made to follow the contour of the perimeters of the lenses. Various other configurations are possible.

FIG. 2C illustrates eyewear 250 that is similar to that illustrated in FIG. 2A, except that the illustrated embodiment includes a unitary or shield-type lens design, in contrast to the dual lens configuration of FIG. 2A. As shown, the unitary or shield-type lens 251 is configured to cover both left and right eyes of the wearer. The unitary or shield-type lens 251 includes a right lens portion 253 and a left lens portion 255, with a bridge portion 257 that is made of the lens material, rather than a separate bridge as in FIG. 2A. Right temple 259 is coupled to the right lateral edge of the right lens portion 253 at connection point 261, and left temple 263 is coupled to the left lateral edge of left lens portion 255 at connection point 265. In some embodiments, a hinge can be positioned at each of connection points 261 and 265, which permits the temples 259 and 263 to be folded inward towards the unitary or shield-type lens 251.

Figure 2D:
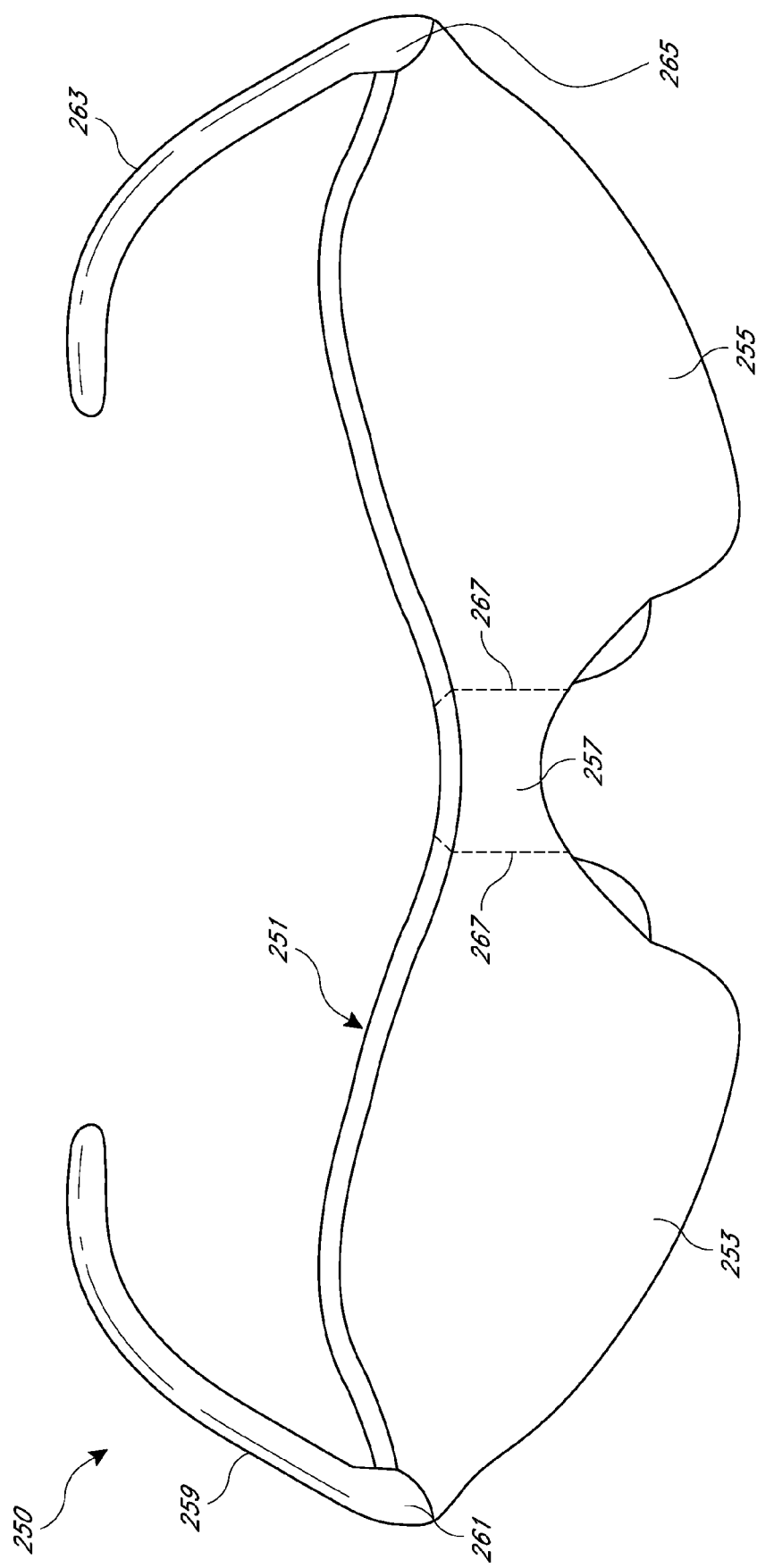
FIG. 2D is a front perspective view of customized eyewear having a unitary or shield-type lens formed of three components.
Figure 3A:
FIG. 3A illustrates front and side images of an individual.
Figure 3B:
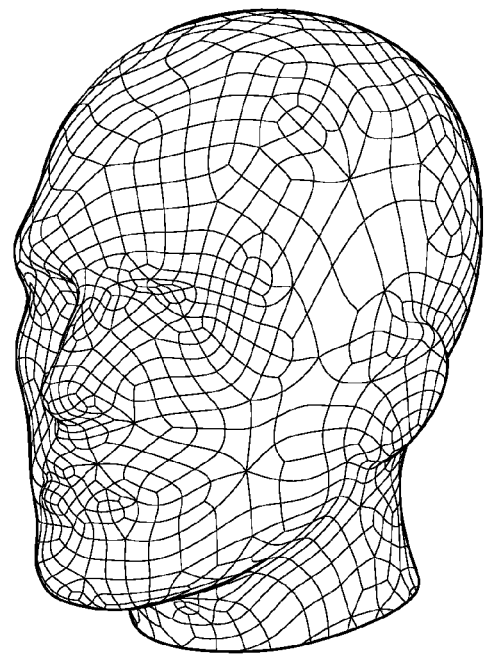
FIG. 3B schematically illustrates a three-dimensional model obtained from the images of FIG. 3A.

FIG. 2D illustrates eyewear 250 that is similar to that illustrated in FIG. 2C, except that the illustrated embodiment includes a unitary or shield-type lens design fabricated by combining three component portions. As illustrated, the right lens portion 253, left lens portion 255, and bridge portion 257 are formed separately, and then joined together along lines 267. In various embodiments, the portions can be joined together by the use of adhesives such as glue, by engagement of complementary structures on the adjacent portions, or by another mechanism. In some embodiments, each of the right lens portion 253, left lens portion 255, and bridge portion 257 may be formed of similar material—for example clear polycarbonate. In some embodiments, one or more of these portions can be formed of a different material or composition. For example, the bridge portion 257 may be tinted with a different hue than the left and right lens portions 255 and 257. The use of separate right and left lens portions 253 and 255 jointed together by a bridge portion 257 can provider certain advantages. For example, in the case of prescription lenses, it can be difficult to produce a unitary or shield-type lens with the appropriate corrective optics for each eye. By forming separate left and right lens portions 253 and 255, appropriate processing can be undertaken to provide the prescribed corrective optics for each eye. These two portions can then be joined together to produce a unitary or shield-type lens from the separately formed components FIGS. 3A-5 illustrate a variety of methods for determining a perimeter of a lens customized for a wearer. With respect to FIGS. 3A and 3B, images of an individual may be obtained and utilized to create a three-dimensional model of the individual's head and/or face. As shown in FIG. 3A, for example, front and side images of an individual can be taken by a camera or other imaging device. Although direct front and side views are illustrated, in other embodiments different views of the individual can be captured. In some embodiments, a video of the individual may be recorded, rather than discrete images. In some embodiments, two or three or more images may be obtained from a variety of angles. FIG. 3B is a schematic illustration of a three-dimensional model obtained from images such as the images of FIG. 3A. Tomography methods for creating three-dimensional models from a plurality of two dimensional images are well known in the art. The three-dimensional model can include the dimensions and shape of certain features of the wearer's face. Using the three-dimensional model, perimeters of left and right lenses can be determined based on selected criteria. For example, as noted above, the lens perimeter may be shaped to follow the contours of the wearer's face, such as the lateral borders of the wearer's nose, the supraorbital arch, lateral and inferior contours of the orbit, etc. Additionally, points at which the lenses are configured to connect to a bridge or temples can also be customized based on size, shape, and location of anatomical features or combinations thereof, such as the wearer's nose bridge and ears. Such shapes and contours can be determined based on the three-dimensional model, thereby permitting lens perimeters to be specifically tailored to a wearer's facial features, without the need for invasive measurement of the wearer's face. In some embodiments, the three-dimensional model can be developed without requiring individual images to be obtained first. For example, a laser scan of an individual's face may be sufficient to generate a three-dimensional model, without the intervening step of obtaining one or more images of an individual's face. Other techniques for generating three-dimensional models may also be used.

In use, an operator may obtain a plurality of images of an individual desiring customized eyewear. The operator may include, but is not limited to, an optometrist, ophthalmologist, nurse, technician, or designer. The images may be utilized by a computer system to develop a three-dimensional model of the individual's head and/or face. In some embodiments, the computer system may automatically generate customized lens perimeters based on the three-dimensional model based on pre-programmed criteria. In some embodiments, the operator and/or individual may provide certain input to the computer system, which may then in turn be used to generate customized lens perimeters. For example, the operator and/or individual may choose to obtain lens perimeters that closely abut the lateral edges of the wearer's nose, while assuming a substantially rectangular shape when viewed directly. These preferences can be provided to the computer system, for example by selection as one of several provided options, or by direct input. The computer system may then use this input and the three-dimensional model to generate customized lens perimeters. In some embodiments, the computer system may allow for the selection of frames, temples, bridges, and other components of the eyewear. As noted above, the design and shape of frames, temples, and other components may themselves take substantially different forms compared to current practice, so as to accommodate and take advantage of the customized lens perimeters as described herein. In various embodiments, any of the frames, temples, bridge and other components may be customized for the wearer.

In some embodiments, the operator may draw on the three-dimensional model to create a customized lens perimeter design. In some embodiments, the individual may collaborate with the operator to create the customized lens perimeter design. An electronic rendition of the customized lenses may be superimposed over an image of the three-dimensional model or other image of the individual. The individual may then elect to modify the lens perimeter design based on his or her review of the superimposed image. In some embodiments, the superimposed image may include a rendition of the completed eyewear, including selected frames, temples, bridges, and the customized lenses. In some embodiments, of these components can be modified by the user or operator as desired to arrive at a final design. In some embodiments, this design may be transmitted, electronically or otherwise, to an optical laboratory. As described in more detail below, the optical laboratory may use the received design to fabricate customized lenses and, in some embodiments, the accompanying frame, temples, bridge, etc.

Figure 4:
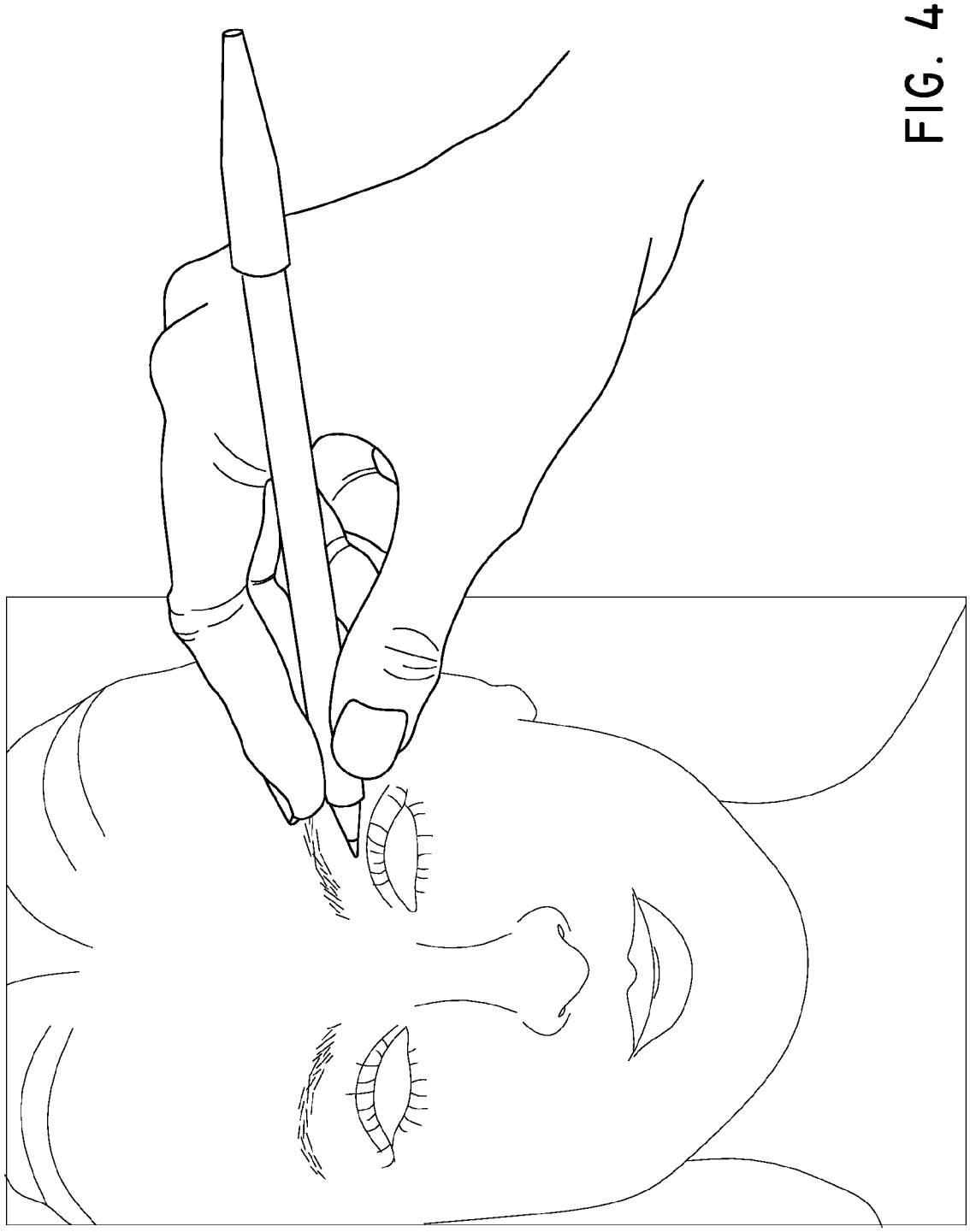
FIG. 4 illustrates an operator manually delineating a lens perimeter on an image of an individual.

FIG. 4 illustrates an operator manually delineating a lens perimeter on an image of an individual. In some embodiments, an image of an intended wearer can be obtained. A desired lens perimeter may then be directly drawn, traced, or otherwise delineated over the image of the intended wearer. In some embodiments, this process can be repeated on multiple images from different views. The lens perimeter may be drawn based on anatomical features as well as stylistic or aesthetic preferences. In some embodiments, the camera may be calibrated such that direct measurements of the dimensions of the face and eyes are not necessary. In some embodiments, for example, the camera used to obtain the image may be placed at a predetermined distance from the individual or include a distance measuring system to determine the distance and assist in performing accurate measurements.

Figure 5A:
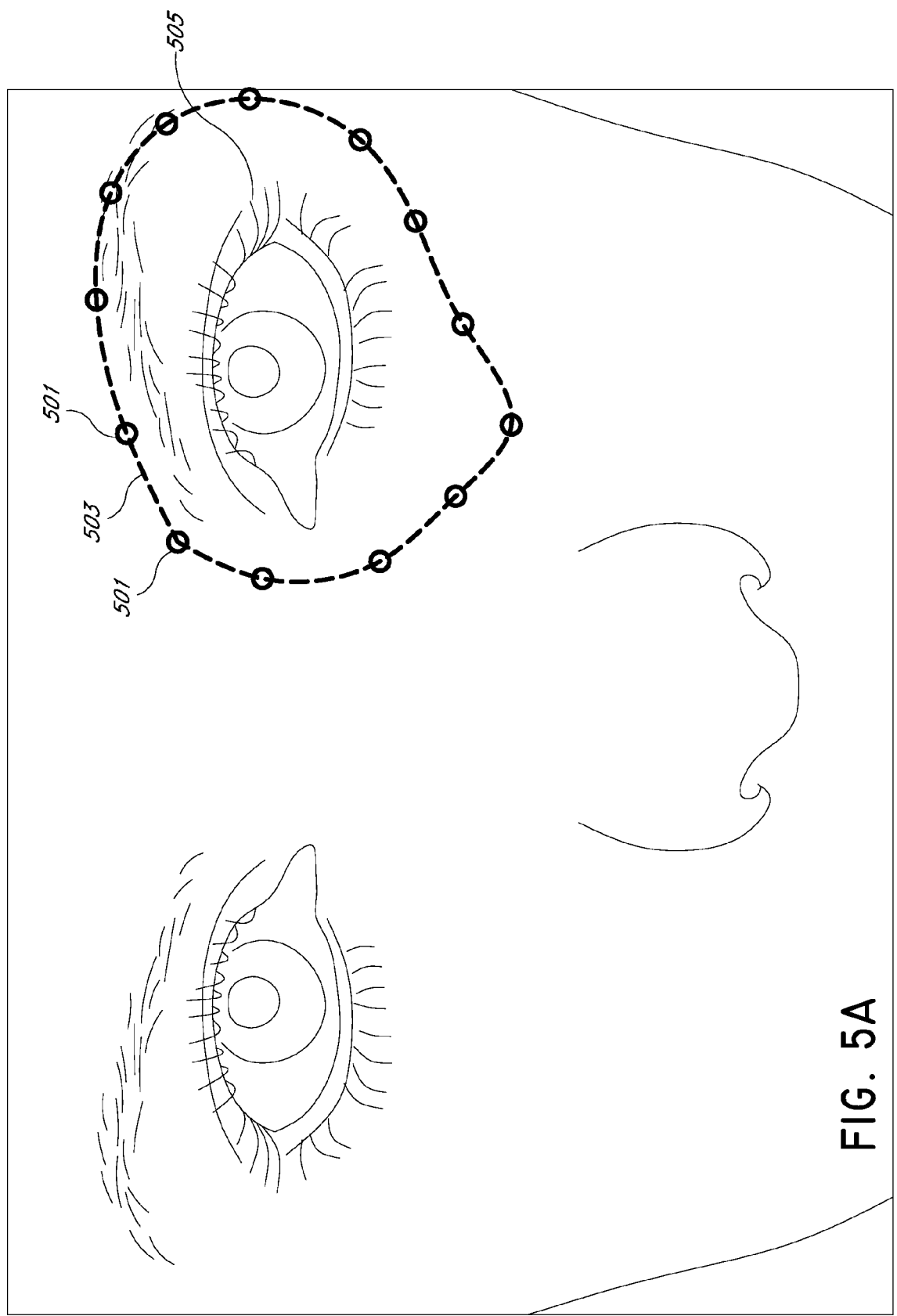
FIG. 5A illustrates a plurality of points delineating a lens perimeter around an eye, according to one embodiment.

FIG. 5A illustrates a plurality of points delineating a lens perimeter around an eye. In some embodiments, the plurality of points 501 forms a line 503 circumscribing the eye 505 of an intended wearer. The line 501 can be extrapolated from a plurality of individual points 503. In some embodiments, each point 503 represents a location nearest the wearer's eye 505 at which the eye 505 is unable to view an object. As such, the line 501 reflects the measured limits of the peripheral vision of the eye 505. The plurality of points 501 can be obtained in a variety of ways. For example, in some embodiments, an object can be placed directly in front of the eye 505. The object can be moved towards the periphery of the eye 505 until the eye 505 can no longer view the object. At such a point 501, the limit of the peripheral vision of the eye 505 is obtained. This can be repeated, moving the object in different directions from the center until a plurality of points 501 have been obtained. Another approach is to move an object from a starting position outside the peripheral vision of the eye 505, and move the object towards the center of the eye 505. The first point at which the eye 505 can view the object can be identified as a point 501, and reflects the measured limit of the peripheral vision of the eye 505 along one direction. This process can be repeated until a plurality of points 501 has been obtained. In some embodiments, a display that moves an object inward or outward from the center of a wearer's field-of-vision can be used to measure the limits of the wearer's peripheral vision.

In some embodiments, a transparent sheet may be placed in front of the eye 505, and the points 501 may be marked directly on the transparent sheet. In some embodiments, the points 501 may be identified via computer on a video recording of the wearer's face. For example, the above measurements can be performed on an individual while video of the individual is being recorded. As the points 501 are identified, they may be electronically marked on the recorded video, and the positions on the points 501 relative to the wearer's face can be stored.

Figure 5B:
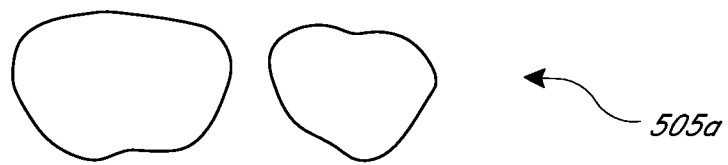
FIG. 5B illustrates a variety of lens perimeters.
Figure 5B:
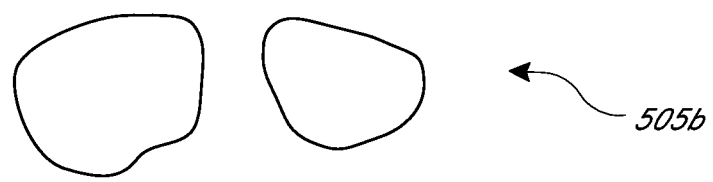
Figure 5B:
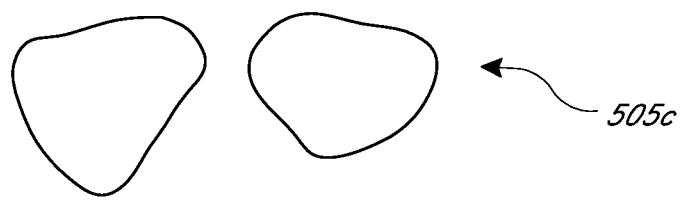
Figure 5B:
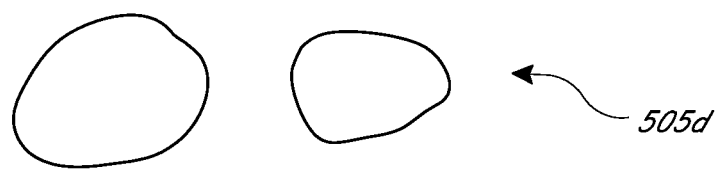
Figure 5B:
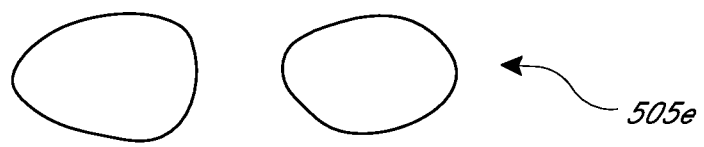

FIG. 5B illustrates a variety of lens perimeters 505a-505e for different intended wearers. Delineating lens perimeters to correspond to the limits of a wearer's peripheral vision can result in a variety of different shapes. Limits of peripheral vision differ among individuals, and accordingly lens perimeters based on these limits can vary widely, as seen in FIG. 5B. Accordingly, as demonstrated by FIG. 5B, lens perimeters can vary widely for different wearers when the lens perimeters are customized for the individual wearer based on some parameters and measurements intrinsic to the wearer. As noted previously, FIG. 5B also shows that in some embodiments the lens perimeters may be symmetrical, while in other embodiments there may be asymmetry between left and right lenses.

Figure 5C:
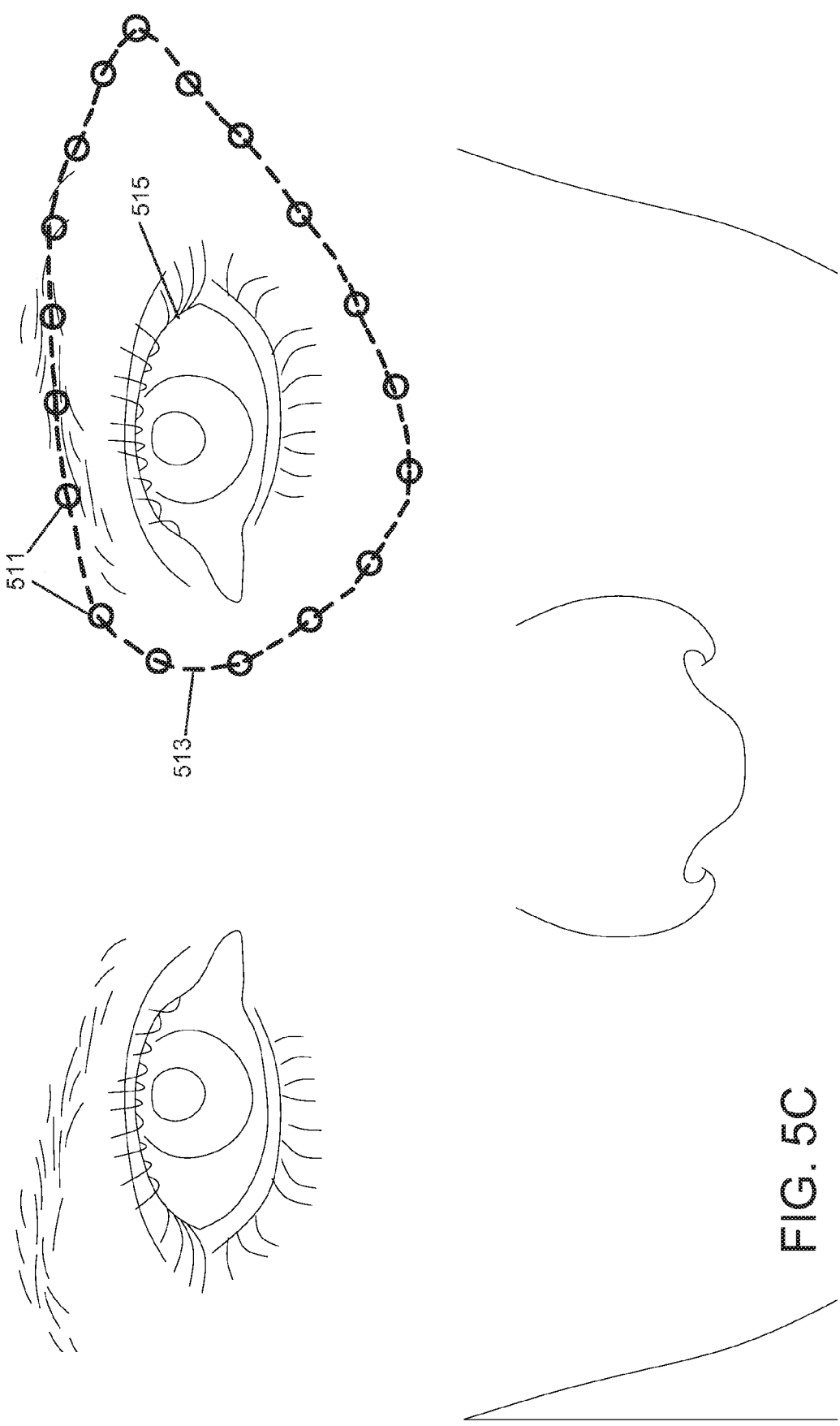
FIG. 5C illustrates a plurality of points delineating a lens perimeter around an eye, according to another embodiment.

FIG. 5C illustrates a plurality of points delineating a lens perimeter around an eye, according to another embodiment. In some embodiments, the plurality of points 511 forms a line 513 circumscribing the eye 515 of an intended wearer. The line 511 can be extrapolated from a plurality of individual points 513, and can define the shape of a lens perimeter. These individual points 513 and the line 511 can be designed such that the lens fits snugly against the face of an intended wearer and blocks wind or particulates from reaching the eye 515. In some embodiments, the lens perimeter corresponding to line 513 of this configuration may encompass a larger area than that of a lens perimeter as described in FIG. 5A, which corresponds to the limits of the peripheral vision of a wearer. In some embodiments, the area encompassed by the lens perimeter 515 of this configuration may be smaller than that of the lens perimeter as described in FIG. 5A. As described above, the lens perimeter can be determined based on anatomical features of a wearer's face. In some embodiments, anatomical features can be used to provide a lens perimeter corresponding to line 513 that blocks substantially all wind, particulates, dust, debris, or other objects from reaching the wearer's eye 515. For example, the lens perimeters can be such that, when worn by the intended wearer, the average distance between the perimeter of each lens and the wearer's face is less than about 5 mm. In some embodiments, the average distance between the perimeter of each lens and the wearer's face may be less than about 5 mm for at least 80% of the perimeters. That is, for at least 80% of the length of each perimeter, the average distance between the perimeter and the wearer's face can be less than 5 mm. In some embodiments, the average distances noted above can be less than about 10 mm, less than about 3 mm, less than about 2 mm, less than about 1 mm, or less than about 0.1 mm. In each case, the distance at any point on the perimeter can be measured as a shortest distance between the point and the wearer's face. In various embodiments, the rim portions of frames may be similarly configured such that an average distance between the rim portion and the wearer's face may be less than about 10 mm, less than about 5 mm, less than about 3 mm, less than about 2 mm, less than about 1 mm, or less than about 0.1 mm.

As the anatomical features of the face can vary widely from one individual to the next, the line 513 may take substantially different shapes for different individuals in order to achieve this effect. In some instances, there may be multiple alternative lens perimeters for a single individual that would achieve the effect of blocking substantially all wind, particulates, etc. from reaching the wearer's eye 515. Lenses in this configuration can be particularly suitable for use during sports or as safety equipment. In some embodiments, such wind-blocking lens perimeters can eliminate the need for goggles.

Figure 6A:
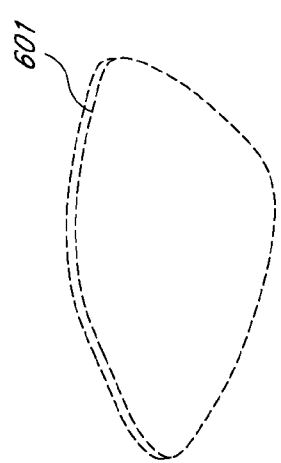
FIG. 6A is a provisional lens perimeter.

FIG. 6A is a provisional lens perimeter. This lens perimeter 601 may be obtained by any of the methods described above. In some embodiments, this provisional lens perimeter 601 can be a set of dimensions that have been determined and recorded, for example specifying the size and contour of the perimeter. In other embodiments, this provisional lens perimeter 601 can take the form of a physical lens that has been fabricated with a given perimeter. In either case, this provisional lens perimeter 601 can be used as a starting point to develop a variety of lens perimeters that differ in one or more ways from the provisional lens perimeter.

Figure 6B:
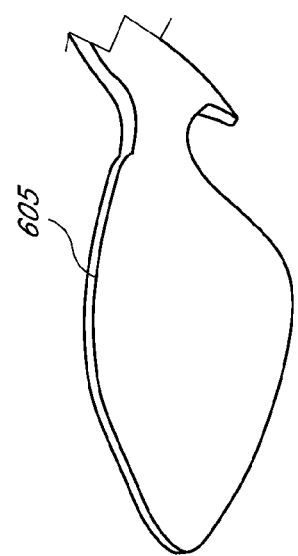
FIGS. 6B-6D are a variety of final lens perimeters based on the provisional lens perimeter of FIG. 6A.
Figure 6C:
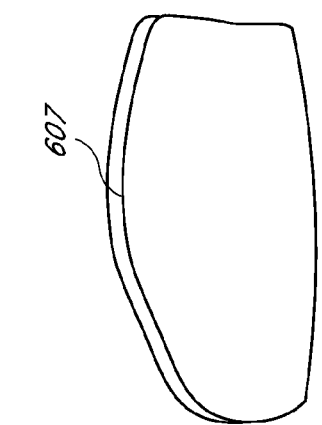
Figure 6D:
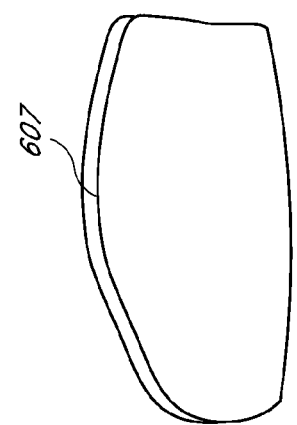

FIGS. 6B-6D are a variety of final lens perimeters based on the provisional lens perimeter of FIG. 6A. For example, the final lens 603 of FIG. 6B is a scaled enlarged implementation of the provisional lens perimeter 601. An operator may first determine a provisional lens perimeter 601 that closely follows the outline of the intended wearer's orbit. However, the intended wearer may desire customized eyewear in which the lenses are of similar shape, but are slightly larger than the determined provisional lens perimeter 601. Accordingly, a scaled enlarged lens 603 can be fabricated based on the wearer's preferences. Of course, in various other embodiments the final lens perimeter can be a scaled shrunken implementation of the provisional lens perimeter. As shown in FIG. 6C, the provisional lens perimeter 601 can assume a unitary or shield-type lens configuration. For example, a provisional lens 601 for one eye may be used (for example, may be mirrored) to provide a provisional lens for the other eye. Alternatively, a separate provisional lens can be determined for each eye. The two provisional lenses may then be used in conjunction to arrive at the final perimeter 605 having a unitary or shield-type lens design. FIG. 6D illustrates another final lens perimeter 607. As illustrated, the inferior edge of the final lens perimeter 607 is substantially flat in comparison to the more curved inferior edge of the provisional lens perimeter 601. This is just one example of changing the shape of a portion of the provisional lens perimeter to arrive at a modified, final lens perimeter. In various embodiments, any portion of the provisional lens perimeter may be modified. Such modifications can include, for example, altering the shape, curvature, slope, or to provide a protrusion or indentation. Such alterations may be used to cover eyebrows, a scar, or a birthmark, etc. Various other modifications to the provisional lens perimeter may be made, including modifications to the curvature, size, or other dimensions or feature.

In some embodiments, a provisional lens perimeter may be determined for each of a wearer's left and right eyes. As noted above, these perimeters may be asymmetrical. If so, then final lens perimeters may either be determined that retain at least some asymmetry, or alternatively the final lens perimeters may be modified with respect to the provisional lens perimeters to arrive at a symmetrical design. For example, the provisional lens perimeters of for left and right eyes can be compared, and one or both can be modified until symmetry is achieved. In some embodiments, the provisional lens perimeters for left and right eyes can be averaged to achieve symmetrical final lens perimeters for left and right eyes. In some embodiments, the provisional lens perimeters for left and right eyes can be only partially averaged or modified, so as to decrease asymmetry without achieving full symmetry between the left and right final lens perimeters. Various other modifications to the determined provisional lens perimeters are possible to arrive at final lens perimeters. These modifications can reflect practical requirements, stylistic choices, or other factors. For example, a particular wearer may prefer lenses to be more or less "pointy", or may desire lenses that rest higher on the face than typical eyewear. Another wearer may prefer lenses to be more square. In some embodiments, the provisional lens perimeters may be enlarged to arrive at the final lens perimeters so as to prevent any air from blowing into a wearer's eyes. Various other such modifications are possible.

Figure 7:
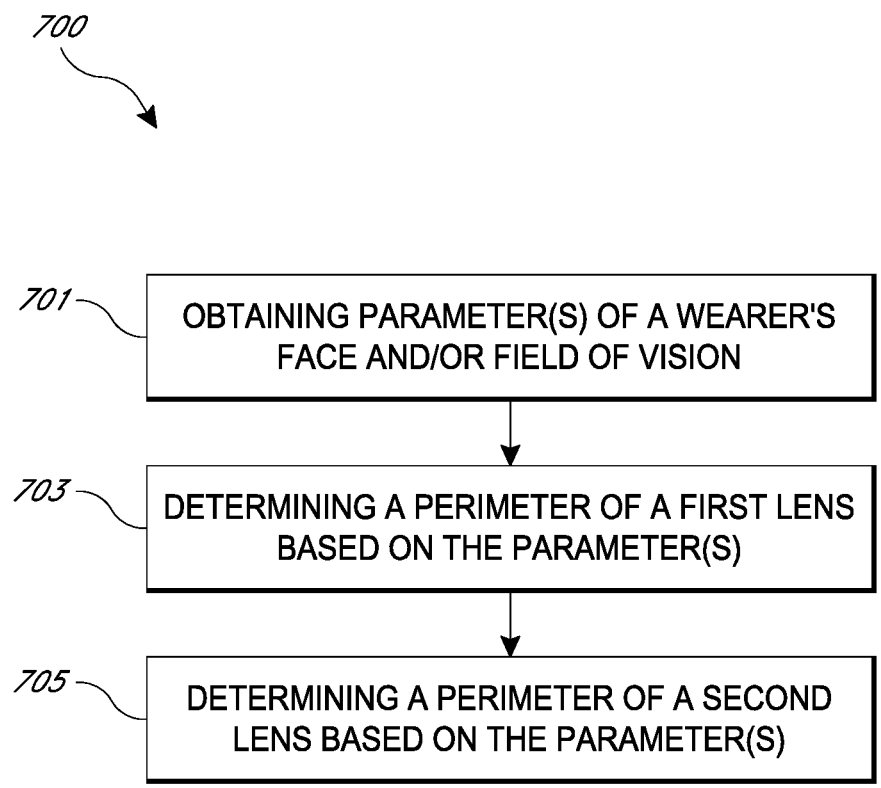
FIG. 7 is a flow diagram illustrating a method of designing customized eyewear.

FIG. 7 is a flow diagram illustrating a method of designing customized eyewear. The process 700 begins with block 701, obtaining one or more parameters of a wearer's face and/or field of vision. As noted above, parameters of a wearer's face can include the shape and dimensions of a wearer's facial features, such as nose, orbit, cheeks, ears, eyebrows, scar, birthmark, etc. Parameters of a wearer's face can be obtained via direct measurement, by developing a three-dimensional model of a wearer's face and/or head, or other approaches. Additionally, any combination of the approaches discussed herein may be used to obtain parameters of a wearer's face. For example, the design process may rely in part computer-based perimeter generation and in part on manual delineation such as hand-drawing to arrive at a customized lens perimeter. Similarly, the design process can rely in part on a measurement of the peripheral vision of the wearer, and in part on manual delineation. In other embodiments, the design process can rely in part on computer-based perimeter generation and in part on measurement of the peripheral vision of the wearer. Any of these approaches may be combined or used in conjunction to arrive at a customized lens perimeter. For example, two or more methods may be used to provide a lens perimeter, followed by an averaging of the lens perimeters provided by each of the methods. As noted above, parameters of a wearer's field of vision can include the delineated limits of a wearer's peripheral vision. Limits of the wearer's peripheral vision can be obtained as described above with respect to FIGS. 5A-B, for example. Other approaches are also possible.

The process 700 continues in block 703 with determining a perimeter of a first lens based on the one or more parameters, and in block 705 with determining a perimeter of a second lens based on the one or more parameters. As noted above, the perimeter of the first and second lenses can be determined in a variety of ways. For example, the lens perimeter can follow certain features of the wearer's face, such as the lateral edge of the nose, the supraorbital ridge, the orbit, etc. In some embodiments, the lens perimeter can correspond to the limits of the wearer's peripheral vision. As described above, in some embodiments, a provisional lens perimeter can be determined for each of the first and second lenses. Then, the provisional lens perimeters can be modified in any number of ways to arrive at a final lens perimeter for each lens. In other embodiments, the final lens perimeter can be determined directly from the obtained parameters of the wearer's face or field of vision. In some embodiments, the perimeters of the first and second lenses can be determined by an operator remotely from the individual for whom the lenses are customized. For example, images of the individual may be taken remotely and transmitted to the operator, electronically or otherwise. The operator may then use the images to determine the perimeters of the lenses as described above (e.g., manually delineating perimeters, generating a three-dimensional model).

Figure 8:
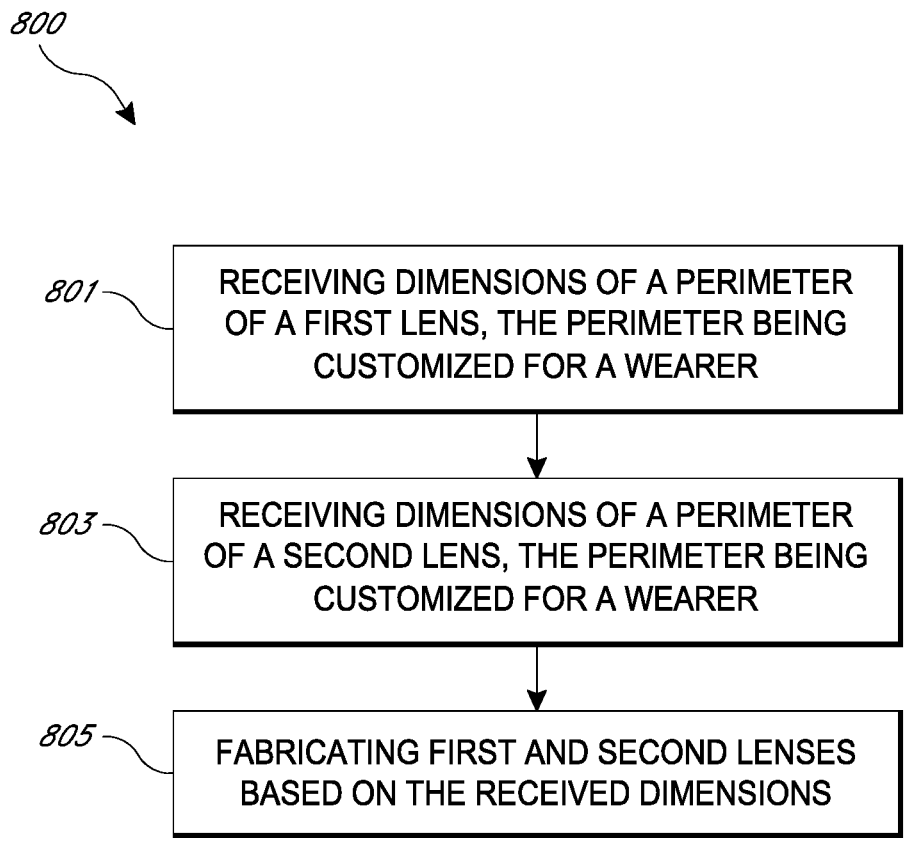
FIG. 8 is a flow diagram illustrating a method of fabricating customized eyewear.

FIG. 8 is a flow diagram illustrating a method of fabricating customized eyewear. The process 800 begins in block 801 with receiving dimensions of a perimeter of a first lens, the perimeter being customized for a wearer. In various embodiments, the dimensions may have been determined by the sender according to one or more of the approaches outlined above. The dimensions may be received as an electronic model of the lens, as measured lens dimensions, as a molded prototype, or other manner. The process 800 continues in block 803 with receiving dimensions of a perimeter of a second lens, the perimeter being customized for a wearer. In block 805 first and second lenses are fabricated based on the received dimensions. The lenses can be fabricated via injection molding, or by successive lens grinding and polishing. Lens grinding can be performed manually or may be automated. As with current lens production techniques, an appropriate blank may be selected. Typically, the blank will already have the front of the lens with a particular curve appropriate for a given optical power. If not, the front of the lens can be ground either manually or via a computer-controlled process. The back surface of the lens is ground to achieve the desired optical power. Additionally cutting around the edges (edging) can be performed until the perimeter of the blank is shaped to the received dimensions.

In some embodiments, the lenses may then be placed into a frame. As noted above, the frame may be rimless or have a full rim. In some embodiments, the frame can be customized for the wearer. For example, required dimensions for the bridge and/or temples can be received, and an appropriate frame fabricated or selected based on the received dimensions. In some embodiments, only less than 10 lenses are fabricated based on the received dimensions. In some embodiments, only less than 5 lenses are fabricated based on the received dimensions.

Figure 9:
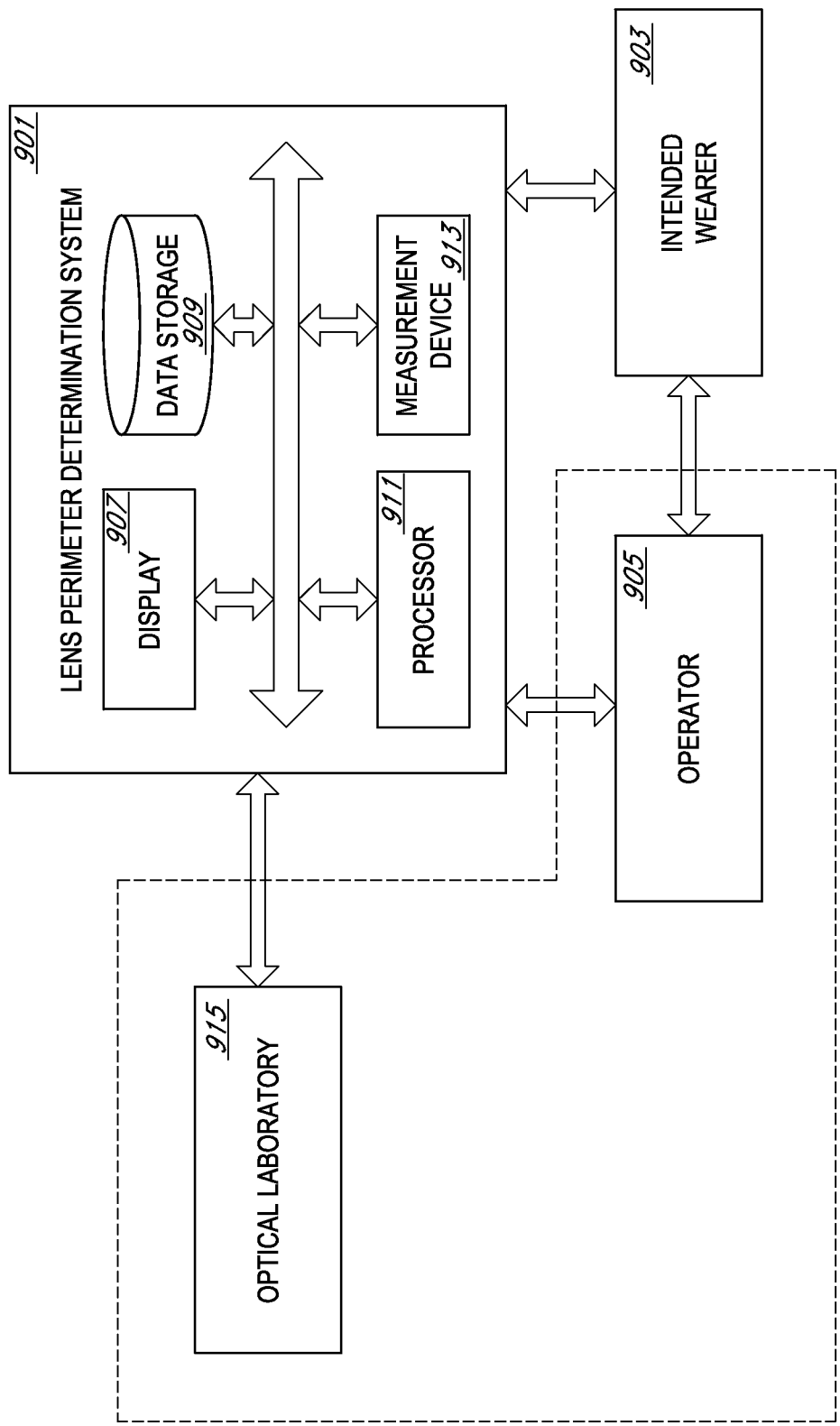
FIG. 9 illustrates an example system architecture for the design and fabrication of customized eyewear.

FIG. 9 illustrates an example system architecture for the design and fabrication of customized eyewear. A lens determination system 901 is configured to interact and communicate with the intended wearer 903 and/or the operator 905. In some embodiments, the lens perimeter determination system 901, intended wearer 903, and operator 905 may all be located within a shared location, for example in an optometrist's office. In other embodiments, as noted above, the intended wearer may be remote from the operator and/or the lens perimeter determination system. The lens perimeter determination system 901 can include a display 907, data storage 909, processor 911, and measurement device(s) 913. The measurement device(s) 913 may include, for example, a camera, laser scanner, or equipment to measure limits of peripheral vision. The measurement device 913 may be used, for example, to obtain certain parameters of the face and/or field of vision of an intended wearer 903. For example, features of the intended wearer's face (e.g., facial curvature, width of head, position of pupils, position of ears, etc. or combinations thereof) may be obtained via the measurement device(s) 913. In some embodiments, limits of the peripheral vision of an intended wearer may be obtained, for example via the method described above with respect to FIGS. 5A-B. These parameters may be stored in data storage 909. The processor 911 may be used to determine lens perimeters based on the obtained parameters from the measurement device(s) 913 such as using methods described herein. In some embodiments, the determined lens perimeters may be graphically displayed to the intended wearer 903 and/or the operator 905 via the display 907. As described above, in some embodiments the lens perimeters may be displayed as superimposed over an image of the intended wearer, and may include selected frames, lens characteristics (e.g., tinted, antireflective coating, polarized, etc.). In some embodiments, the intended wearer 903 and/or the operator 905 may manipulate the determined lens perimeters by interacting with the lens determination system 901. For example, the intended wearer 903 may view the displayed lens perimeters via the display 907, and determine that an alternative shape would be desirable. The intended wearer 903 may then manipulate the determined lens perimeters to arrive at a desired final lens perimeter, including shape of lens, locations for attachment to bridge and temples, etc. A desired frame may likewise be selected by the intended wearer 903 or the operator 905. The final lens dimensions and selected frame may be stored in data storage 909.

Optical laboratory 915 may also be in communication with the lens perimeter determination system 901. The dashed line indicates that, in some embodiments, the operator 905 and optical laboratory 915 may be the same person or entity, as described in more detail below. In some embodiments, the operator 905 and the optical laboratory 915 can be separate and distinct entities. The final lens dimensions stored in data storage 909 may be transmitted to the optical laboratory 915 in response to instructions from the intended wearer 903 or the operator 905. The dimensions may for example be transmitted via a network (e.g., internet, intranet, e-mail) or other avenues. The optical laboratory 915 may then make lenses based on the received dimensions, for example by surfacing (grinding), edging, and polishing pre-formed blanks, by molding, or other methods. Optical laboratory 915 may then place the customized lenses into a frame. In some embodiments, the customized lenses may be placed into a frame by the user 905 or the intended wearer 903. In some embodiments, the customized lenses may be placed into a frame by a third-party eyewear assembler.

As discussed above, various parameters of the eyewear, such as the location of the bridge and the temples with respect to the lens may be customized for the individual wearer. The optical laboratory, operator, and wearer, or combinations thereof, may contribute to selection of these parameters. For example, the operator may decide that the bridge and/or temples need to be higher, lower, more temporal or more nasal, and communicate such information to the optical laboratory 915. The optical laboratory 915 may use these customized frame or assembly specifications to drill holes or otherwise connect the bridge and temples to the lens or otherwise configure the eyewear.

In some embodiments, the frame is selected by the intended wearer 903 and/or the operator 905 and stored in data storage 909. The selected frame may be communicated to the optical laboratory 915.

In some embodiments, a frame supplier may provide a selection of possible frames to the lens perimeter determination system 901 so that the intended wearer 903 and/or the operator 905 may choose a desired frame from among those provided by the frames supplier. For example, the frame supplier may provide a selection of possible frames electronically to the lens perimeter determination system 901 to be stored in data storage 909. These possible frames may then be displayed to the intended wearer 903 and the operator 905 via the display 907. As noted above, selected frames may be displayed along with the customized lenses, in some instances overlaid on top of an image of the intended wearer 903. Once the optical laboratory 915 has fitted the customized lenses to the desired frames, the assembled eyewear is sent to the intended wearer 903 or the operator 905. In some embodiments, the operator 905 may then make final adjustments to the assembled eyewear. As noted above, in some embodiments, the lenses may be placed into a frame by the intended wearer 903 or the operator 905. In other embodiments, the perimeter determination system 901 may access databases of frame suppliers (not shown in FIG. 9) who may not be the frame assemblers. The operator may, for example, with input from the wearer, search databases of one or more suppliers, select a suitable frame, and communicate that information to the supplier to provide the frame. In some embodiments, different bridges, temples or other frame components may be interchanged and/or selected by the wearer with the help of the operator. The frame assembler may obtain the frame or selected components directly from the supplier in some embodiments, although the operator may also relay the frame to the frame assembler. A wide variety of configurations are possible.

The lens perimeter determination system 901 may be coupled via a network (e.g., the Internet) to one or more of the intended wearer 903, the operator 905, and the optical laboratory 915. The system 901 may be accessed by any of these parties via computer systems, mobile smart phones, electronic reader, pads, interactive television sets/set top boxes, as well as other devices known in the art or yet to be devised. The system 901 may be accessed wirelessly, via wired broadband connection, or via a public switched telephone network, by way of example.

In some embodiments, a variety of prescription or non-prescription clear lenses may be supplied to the operator 905. The supplied lenses may include a variety of different curvature options, for example covering all curvature options from 0 base curve to 10 base curve. The operator 905 may then employ an edging machine to cut or edge a selected lens to a customized perimeter. In some embodiments, the lens selection is based on the curvature of the wearer's face. In some embodiments, the operator 905 may input certain parameters of a wearer's face and/or field of vision into the edging machine. The machine may then automatically determine the appropriate lens curvature to be selected. The machine may then automatically cut or edge a desired lens perimeter using lens designs having the preselected curvature. In some embodiments, the newly cut or edged lenses may then be placed on the wearer, after which the operator 905 may make any necessary adjustments. In this approach, the operator 905 may assume the additional role of the optical laboratory 915 by use of the machine. In some embodiments, the operator 905 may additionally assume the role of the eyewear assembler, by placing the newly cut lenses into an appropriate frame.

In some embodiments, completed lenses may be sent to an optical laboratory, which can coat the lenses or use the completed lenses as a standard to fabricate a similar lens. A final assembled eyewear product can be produced, as described with respect to FIG. 9 above.

In other embodiments, the completed lenses may already be assembled into completed eyewear by the operator on-site. For example, in some embodiments the selected lenses may already include a desired prescription, optical coatings, or other features. The operator may use the edging machine to cut or edge the selected lenses to a customized perimeter. The customized lenses may then be drilled and assembled with a frame (for example temples and a bridge, in the case of rimless eyewear). Any necessary adjustments may be made by the operator throughout the process. Unless otherwise indicated, the functions described herein may be performed by software (e.g., including modules) including executable code and instructions running on one or more systems including one or more computers, such as barcode and/or other authentication computer systems. The software may be stored in computer readable media (e.g., some or all of the following: optical media (e.g., CD-ROM, DVD, Blu-ray, etc.), magnetic media (e.g., fixed or removable magnetic media), semiconductor memory (e.g., RAM, ROM, Flash memory, EPROM, etc.), and/or other types of computer readable media.

The one or more computers can include one or more central processing units (CPUs) that execute program code and process data, non-transitory, tangible memory, including for example, one or more of volatile memory, such as random access memory (RAM) for temporarily storing data and data structures during program execution, non-volatile memory, such as a hard disc drive, optical drive, or FLASH drive, for storing programs and data, including databases, a wired and/or wireless network interface for accessing an intranet and/or Internet, and/or other interfaces.

In addition, the computers can include a display for displaying user interfaces, data, and the like, and one or more user input devices, such as a keyboard, mouse, pointing device, touch screen, microphone and/or the like, used to navigate, provide commands, enter information, provide search queries, and/or the like. The systems described herein can also be implemented using general-purpose computers, special purpose computers, terminals, state machines, and/or hardwired electronic circuits.

Various embodiments provide for communications between one or more systems and one or more users. These user communications may be provided to a user terminal (e.g., an Interactive television, a phone, a video game system, a laptop/desktop computer, a device providing Internet access, or other networked device). For example, communications may be provided via Webpages, downloaded documents, email, SMS (short messaging service) message, MIMS (multimedia messaging service) message, terminal vibrations, other forms of electronic communication text-to-speech message, otherwise.

Various modifications to the embodiments described in this disclosure may be readily apparent to those skilled in the art, and the principles defined herein may be applied to other embodiments without departing from the spirit or scope of this disclosure. Thus, the claims are not intended to be limited to the embodiments shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be described as occurring in a particular order, this should not be understood as requiring that such operations be performed in the particular order described or in sequential order, or that all described operations be performed, to achieve desirable results. Further, other operations that are not disclosed can be incorporated in the processes that are described herein. For example, one or more additional operations can be performed before, after, simultaneously, or between any of the disclosed operations. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single product or packaged into multiple products. Additionally, other embodiments are within the scope of the following claims. In some cases, the actions recited in the claims can be performed in a different order and still achieve desirable results.

What is claimed is:

1. Customized eyewear comprising:
a first lens having a front surface, a back surface, and a perimeter, wherein the perimeter is customized for a wearer;
a second lens having a front surface, a back surface, and a perimeter, wherein the perimeter is customized for the wearer; and
a frame, said first and second lenses attached to said frame, wherein the frame is customized for the wearer, wherein the perimeter of the first lens or the second lens is customized based on extraction of a plurality of points taken in three-dimensional space.

2. The customized eyewear of claim 1, wherein the perimeters of the first and second lenses are each customized for the wearer on the basis of one or more of:
peripheral vision of the wearer; and
curvature of the wearer's face in three-dimensional space.

3. The customized eyewear of claim 2, wherein the perimeters of the first and second lenses are each further customized for the wearer on the basis of non-physical attributes of a wearer.

4. The customized eyewear of claim 1, wherein the eyewear is rimless.

5. The customized eyewear of claim 1, wherein the frame comprises a bridge and temples and is configured to support the first and second lenses in front of at least a portion of the wearer's face in a first position.

6. The customized eyewear of claim 5, wherein in the first position at least one of the first and second lenses is in contact with the wearer's face.

7. The customized eyewear of claim 5, wherein the first and second lenses are configured such that when the frame is in the first position, the wearer cannot view the perimeter of the first lens or the perimeter of the second lens.

8. The customized eyewear of claim 5, wherein the first and second lenses are configured such that when the frame is in the first position, the wearer's eyes are shielded from substantially all wind or particulates.

9. The customized eyewear of claim 5, wherein the first and second lenses are configured such that when the frame is in the first position, an average distance between the perimeters and the wearer's face is less than about 5 mm,
wherein the distance at any point on the perimeters is measured as a shortest distance between the point and the wearer's face.

10. The customized eyewear of claim 9, wherein the average distance between the perimeters and the wearer's face is less than about 1 mm.

11. The customized eyewear of claim 5, wherein the first and second lenses are configured such that when the frame is in the first position, the distance between the perimeters and the wearer's face is less than about 5 mm for at least 80% of the perimeters,
wherein the distance at any point on the perimeters is measured as a shortest distance between the point and the wearer's face.

12. The customized eyewear of claim 5, wherein the frame comprises a rim portion configured such that when the frame is in the first position, an average distance between the rim portion and the wearer's face is less than about 5 mm,
wherein the distance at any point on the rim portion is measured as a shortest distance between the point and the wearer's face.

13. The customized eyewear of claim 12, wherein the average distance between the rim portion and the wearer's face is less than about 1 mm.

14. The customized eyewear of claim 1, wherein the perimeter of the first lens encloses a larger or smaller area than the perimeter of the second lens.

15. The customized eyewear of claim 1, wherein the first lens and the second lens are asymmetrical with respect to one another.

16. The customized eyewear of claim 1, wherein the first lens and the second lens are connected by a customizable nose piece.

17. The customized eyewear of claim 1, wherein the perimeter of the first lens or the second lens is a closed loop in three-dimensional space.

18. The customized eyewear of claim 1, wherein the perimeter of the first lens or the second lens comprises a plurality of points that circumscribes an eye of the wearer at which the eye is unable to view an object.

19. The customized eyewear of claim 1, wherein the perimeters of the first and second lenses are each customized for the wearer on the basis of curvature of the wearer's face in three-dimensional space.

20. The customized eyewear of claim 1, wherein the perimeters of the first lens and the second lens are customized based on a three-dimensional model of the wearer's head and/or face.

21. The customized eyewear of claim 1, wherein the frame is customized such that the eyewear fits the face of the wearer.

22. The customized eyewear of claim 1, wherein the frame comprises rim portions.

23. The customized eyewear of claim 22, wherein the average distance between the rim portions and the face is less than 5 mm.

24. The customized eyewear of claim 22, wherein the average distance between the rim portions and the face is less than 3 mm.

25. The customized eyewear of claim 22, wherein the average distance between the rim portions and the face is less than 2 mm.

26. The customized eyewear of claim 22, wherein frame comprises full rims.

27. The customized eyewear of claim 1, wherein the frame comprises bridges and the location of the bridges with respect to the lens is customized.

28. The customized eyewear of claim 1, wherein the frame comprises temples and the location of the temples with respect to the lens is customized.

29. A method for producing customized eyewear, the method comprising:
obtaining one or more parameters of a wearer's face or field of vision;
determining a perimeter of a first lens based on the one or more parameters; and
determining a perimeter of a second lens based on the one or more parameters,
wherein determining the perimeters of the first and second lenses comprises:
determining a provisional perimeter of the first lens;
determining a provisional perimeter of the second lens;
comparing the provisional perimeters of the first and second lenses;
determining a final perimeter of a first lens based on the comparison; and
determining a final perimeter of the second lens based on the comparison,
thereby obtaining data for the customization of at least said first and second lenses, wherein said obtaining data for said customization of at least said first and second lens is based on extraction of a plurality of points taken in three-dimensional space and does not require the wearer to wear eyewear.

30. The method of claim 29, further comprising storing the determined perimeters of the first and second lenses.

31. The method of claim 30, further comprising transmitting the stored perimeters to an optical laboratory.

32. The method of claim 29, further comprising fabricating the first and second lenses based on the determination of the perimeters.

33. The method of claim 29,
wherein the provisional perimeters of the first and second lenses are asymmetrical with respect to one another, and
wherein the final perimeters of the first and second lenses are symmetrical with respect to one another.

34. The method of claim 29, wherein determining the final perimeters of the first and second lenses comprises obtaining an average of the provisional perimeters of the first and second lenses.

35. The method of claim 29, wherein determining the final perimeters of the first and second lenses comprises adjusting the provisional perimeters based on non-physical attributes of the wearer.

36. The method of claim 29, wherein said one or more parameters comprise one or more of:
contours of the wearer's nose;
curvature of the wearer's face in three-dimensional space; and
contours of the wearer's orbits.

37. The method of claim 29, further comprising using images of the wearer's face to create a three-dimensional model of the wearer's face.

38. The method of claim 29, wherein obtaining one or more parameters comprises obtaining an image of the wearer's face, and wherein determining the perimeters of the first and second lenses comprises delineating the perimeters with respect to the obtained image.

39. The method of claim 38, wherein delineating the perimeters comprises drawing the perimeters over the obtained image.

40. The method of claim 29, wherein obtaining one or more parameters comprises measuring the peripheral vision of an eye of the wearer.

41. The method of claim 40, wherein measuring the peripheral vision comprises identifying a point at which the eye cannot view an object positioned about the periphery of the field of vision of the eye.

42. The method of claim 41, wherein the point is at a position nearest the eye's field of vision at which the eye cannot view the object.

43. The method of claim 42, wherein measuring the peripheral vision comprises identifying a plurality of such points, and extrapolating to develop a line circumscribing the eye, the line defining a boundary of the field of vision of the eye.

44. The method of claim 43, wherein the perimeter of the first lens corresponds to the line.

45. Customized eyeglasses made according to the method of claim 29.

46. The method of claim 29, wherein the parameters are based on the wearer's measured field of vision.

47. The method of claim 46, wherein the field of vision is determined using (1) a series of points determined by moving an object inward or outward in the wearer's field of vision or (2) a display that moves an object inward or outward from the center of a wearer's field of vision.

48. The method of claim 29, wherein the determined perimeter of the first lens or the second lens is a closed loop in three-dimensional space.

49. The method of claim 29, wherein the determined perimeter of the first lens or the second lens comprises a plurality of points that circumscribes an eye of the wearer at which the eye is unable to view an object.

50. The method of claim 29, wherein the perimeters of the first and second lenses are each customized for the wearer on the basis of curvature of the wearer's face in three-dimensional space.

51. The method of claim 29, wherein the perimeters of the first lens and the second lens are customized based on a three-dimensional model of the wearer's head and/or face.

52. A method for producing customized eyewear, the method comprising:
receiving dimensions of a perimeter of a first lens, the perimeter being customized for a wearer, wherein the dimensions were obtained based on extraction of a plurality of points taken in three-dimensional space without requiring the wearer to wear eyewear;
receiving dimensions of a perimeter of a second lens, the perimeter being customized for the wearer, wherein the dimensions were obtained based on extraction of a plurality of points taken in three-dimensional space without requiring the wearer to wear eyewear; and
fabricating first and second lenses based on the received dimensions, and
assembling the first and second lenses in a frame, wherein the frame is customized for the wearer.

53. The method of claim 52, wherein the perimeters of the first and second lenses are determined based on one or more parameters of a wearer's face or field of vision.

54. The method of claim 52, comprising fabricating only less than 10 lenses based on the received dimensions.

55. The method of claim 52, comprising fabricating only less than 5 lenses based on the received dimensions.

56. The method of claim 52, wherein the perimeter of the first lens or the second lens is a closed loop in three-dimensional space.

57. The method of claim 52, wherein the perimeter of the first lens or the second lens comprises a plurality of points that circumscribes an eye of the wearer at which the eye is unable to view an object.

58. The method of claim 52, wherein the perimeters of the first and second lenses are each customized for the wearer on the basis of curvature of the wearer's face in three-dimensional space.

59. The method of claim 52, wherein the perimeters of the first lens and the second lens are customized based on a three-dimensional model of the wearer's head and/or face.

60. A method for producing customized eyewear, the method comprising:
obtaining one or more parameters of a wearer's face or field of vision;
determining a perimeter of a first lens based on the one or more parameters; and
determining a perimeter of a second lens based on the one or more parameters,
thereby obtaining data for the customization of at least said first and second lenses, wherein said obtaining involves extraction from a plurality of points taken in three dimensional space, and
determining dimensions of a frame that are customized for the wearer.

61. The method of claim 60, wherein the parameters are based on the wearer's field of vision.

62. The method of claim 60, wherein the determined perimeter of the first lens or the second lens is a closed loop in three-dimensional space.

63. The method of claim 60, wherein the determined perimeter of the first lens or the second lens comprises a plurality of points that circumscribes an eye of the wearer at which the eye is unable to view an object.

64. The method of claim 60, wherein the perimeters of the first and second lenses are each customized for the wearer on the basis of curvature of the wearer's face in three-dimensional space.

65. The method of claim 60, wherein the perimeters of the first lens and the second lens are customized based on a three-dimensional model of the wearer's head and/or face.

66. The method of claim 60, wherein the frame is customized such that the eyewear fits the face of the wearer.

67. The method of claim 60, wherein the frame comprises rim portions.

68. The method of claim 67, wherein the average distance between the rim portions and the face is less than 5 mm.

69. The method of claim 67, wherein the average distance between the rim portions and the face is less than 3 mm.

70. The method of claim 67, wherein the average distance between the rim portions and the face is less than 2 mm.

71. The method of claim 67, wherein the frame comprise full rims.

72. The method of claim 60, wherein the frame comprises bridges and the location of the bridges with respect to the lens is customized.

73. The method of claim 60, wherein the frame comprises temples and the location of the temples with respect to the lens is customized.

74. Customized eyewear comprising:
- a first lens having a front surface, a back surface, and a perimeter, wherein the perimeter is customized for a wearer; and
- a second lens having a front surface, a back surface, and a perimeter, wherein the perimeter is customized for the wearer,
- wherein the perimeter of the first lens or the second lens is customized based on extraction of a plurality of points taken in three-dimensional space and a comparison of provisional perimeters for the first and second lenses.

75. The customized eyewear of claim 74, wherein the first lens has optical power.

76. The customized eyewear of claim 74, wherein the perimeter of the first lens or the second lens is a closed loop in three-dimensional space.

77. The customized eyewear of claim 74, wherein the perimeter of the first lens or the second lens comprises a plurality of points that circumscribes an eye of the wearer at which the eye is unable to view an object.

78. The customized eyewear of claim 74, wherein the perimeters of the first and second lenses are each customized for the wearer on the basis of curvature of the wearer's face in three-dimensional space.

79. The customized eyewear of claim 74, wherein the perimeters of the first lens and the second lens are customized based on a three-dimensional model of the wearer's head and/or face.

* * * * *